United States Patent
Kimmel et al.

(10) Patent No.: US 8,986,264 B2
(45) Date of Patent: Mar. 24, 2015

(54) TRANSSEPTAL NEEDLE APPARATUS

(71) Applicant: Greatbatch Ltd., Clarence, NY (US)

(72) Inventors: Scott Kimmel, St Paul, MN (US); Kevin Pietsch, Greenfield, MN (US); Rodolphe Katra, Blaine, MN (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 13/887,768

(22) Filed: May 6, 2013

(65) Prior Publication Data

US 2013/0303997 A1    Nov. 14, 2013

Related U.S. Application Data

(60) Provisional application No. 61/644,180, filed on May 8, 2012.

(51) Int. Cl.
*A61M 39/10* (2006.01)
*A61B 17/34* (2006.01)
(Continued)

(52) U.S. Cl.
CPC ........ *A61M 39/1011* (2013.01); *A61B 17/3439* (2013.01); *A61B 18/1477* (2013.01); *A61B 18/18* (2013.01); *A61B 17/3478* (2013.01); *A61B 2017/00247* (2013.01); *A61B 2018/1425* (2013.01); *A61M 2025/0079* (2013.01); *A61B 2019/304* (2013.01); *A61B 2019/481* (2013.01); *A61B 2218/007* (2013.01)
USPC ...................... 604/264; 604/164.01; 606/167

(58) Field of Classification Search
CPC . A61M 25/06; A61M 29/00; A61M 39/1011; A61B 17/3439; A61B 18/18
USPC ............. 604/164.01–164.14, 165.01–165.04, 604/248, 250, 264, 533; 606/167
See application file for complete search history.

(56) References Cited

U.S. PATENT DOCUMENTS

| | | | |
|---|---|---|---|
| 4,747,823 A | 5/1988 | Buchanan | |
| 5,429,616 A | 7/1995 | Schaffer | |

(Continued)

FOREIGN PATENT DOCUMENTS

| | | |
|---|---|---|
| DE | 10004385 | 8/2001 |
| EP | 0455478 | 11/1991 |

(Continued)

OTHER PUBLICATIONS

EP Search dated May 7, 2014 for EP Application No. 13167149.7.

(Continued)

*Primary Examiner* — Theodore Stigell
*Assistant Examiner* — Amber Stiles
(74) *Attorney, Agent, or Firm* — Michael P. Horvath

(57) ABSTRACT

In various examples, an apparatus includes a gripping member including a body and a gripping portion attached to the body. The body includes a passage configured to accept a needle cannula within the passage. The gripping portion includes an open configuration in which the needle cannula is movable within the passage and a closed configuration in which the gripping portion engages the needle cannula to inhibit movement of the needle cannula within the passage. A coupling member is rotatably attached to the gripping member. The coupling member is configured to selectively couple with a dilator. The coupling member includes a bore fluidly coupled with the passage, the bore being configured to accept the needle cannula within the bore.

20 Claims, 12 Drawing Sheets

(51) Int. Cl.
*A61B 18/14* (2006.01)
*A61B 18/18* (2006.01)
*A61B 17/00* (2006.01)
*A61M 25/00* (2006.01)
*A61B 19/00* (2006.01)

(56) References Cited

U.S. PATENT DOCUMENTS

| | | | |
|---|---|---|---|
| 5,454,790 A * | 10/1995 | Dubrul | 604/104 |
| 5,578,052 A | 11/1996 | Koros et al. | |
| 5,782,807 A * | 7/1998 | Falvai et al. | 604/164.1 |
| 5,861,002 A | 1/1999 | Desai | |
| 6,063,081 A | 5/2000 | Mulier et al. | |
| 6,096,024 A | 8/2000 | Graves et al. | |
| 6,217,554 B1 | 4/2001 | Green | |
| 6,298,256 B1 | 10/2001 | Meyer | |
| 6,585,694 B1 | 7/2003 | Smith et al. | |
| 6,723,082 B1 | 4/2004 | Payne et al. | |
| 7,001,396 B2 * | 2/2006 | Glazier et al. | 606/108 |
| 8,016,784 B1 | 9/2011 | Hayzelden et al. | |
| 2002/0010416 A1 | 1/2002 | Uflacker | |
| 2002/0183738 A1 | 12/2002 | Chee et al. | |
| 2003/0100862 A1 | 5/2003 | Edwards et al. | |
| 2003/0187460 A1 | 10/2003 | Chin et al. | |
| 2004/0143262 A1 | 7/2004 | Visram et al. | |
| 2004/0147877 A1 | 7/2004 | Heuser | |
| 2005/0149097 A1 | 7/2005 | Regnell et al. | |
| 2005/0277889 A1 | 12/2005 | Neidert et al. | |
| 2006/0155246 A1 * | 7/2006 | Higuchi et al. | 604/165.01 |
| 2007/0270751 A1 | 11/2007 | Stangenes et al. | |
| 2008/0161792 A1 | 7/2008 | Wang et al. | |
| 2008/0262318 A1 * | 10/2008 | Gorek et al. | 600/235 |
| 2008/0262430 A1 * | 10/2008 | Anderson et al. | 604/164.1 |
| 2009/0105742 A1 | 4/2009 | Kurth et al. | |
| 2009/0171276 A1 | 7/2009 | Bednarek et al. | |

FOREIGN PATENT DOCUMENTS

| | | |
|---|---|---|
| EP | 1462141 | 9/2004 |
| EP | 1683543 | 7/2006 |
| EP | 1736108 | 12/2006 |
| EP | 1857135 | 11/2007 |
| WO | 02/32335 | 4/2000 |
| WO | 00/56238 | 9/2000 |
| WO | 03077982 | 9/2003 |
| WO | 2005018732 | 3/2005 |
| WO | 2006/138462 | 12/2006 |
| WO | 2012/125239 | 9/2012 |

OTHER PUBLICATIONS

Partial European Search Report for Application 13167145.5 dated Dec. 12, 2013.
Kimmel, Scott et al., "Transseptal Needle Apparatus Search Report".
Ross J., Jr.: Transseptal left heart catheterization a 50-year odyssey. Journal of the American College of Cardiology. 2008; 51: 2107-2115. Doi: 10.1016/j.jacc.2007.12.060.
Cope, C.: Newer Techniques of Transseptal Left-Heart Catheterization. Circulation Journal of the American Heart Association. 1963; 27: 758-761. Doi: 10.1161/01.Cir.27.4.758.
Feld GK, Tiongson J, Oshodi G.: Particle formation and risk of embolization during transseptal catheterization: comparison of standard transseptal needles and a new radiofrequency transseptal needle. J Interv Card Electrophsiol. Jan. 2011; 30(1): 31-6.
Sangiorgi G, Colombo A.; Embolic protection devices: Heart. Sep. 2003; 89(9): 990-992.

* cited by examiner

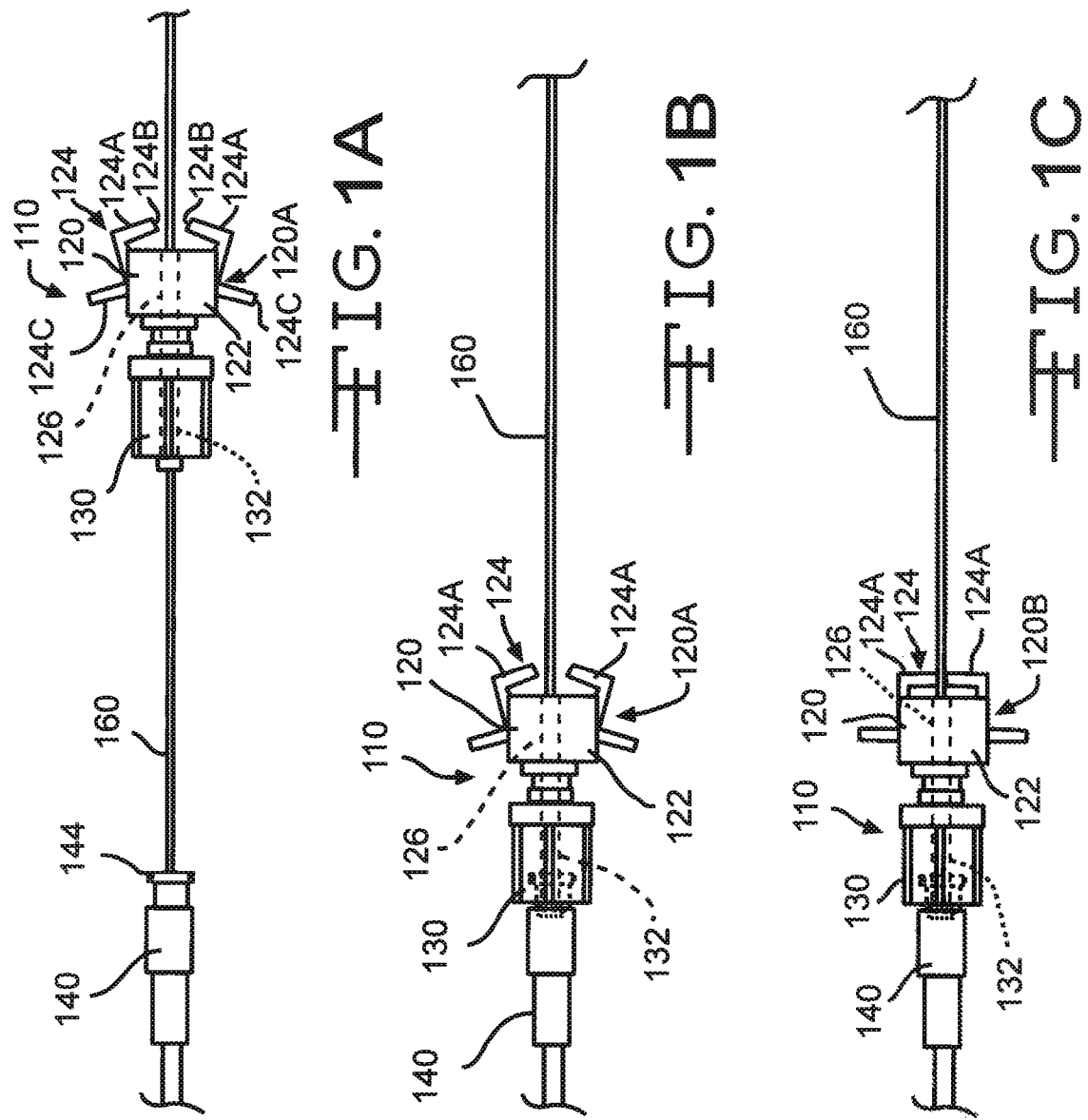

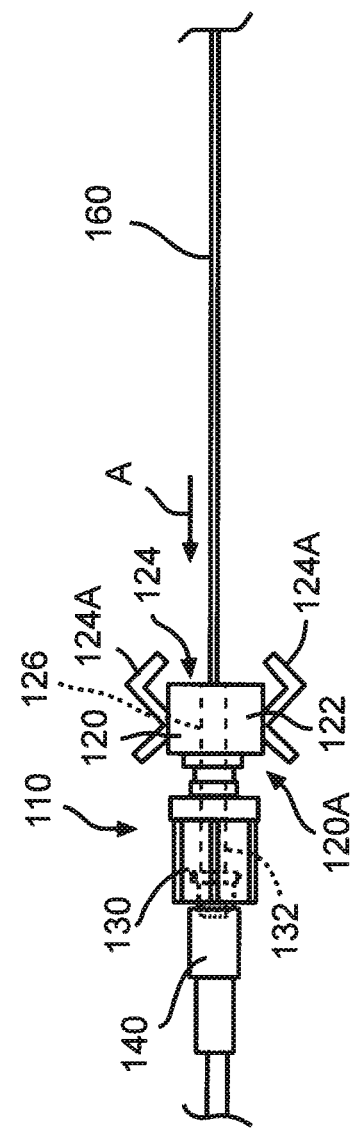

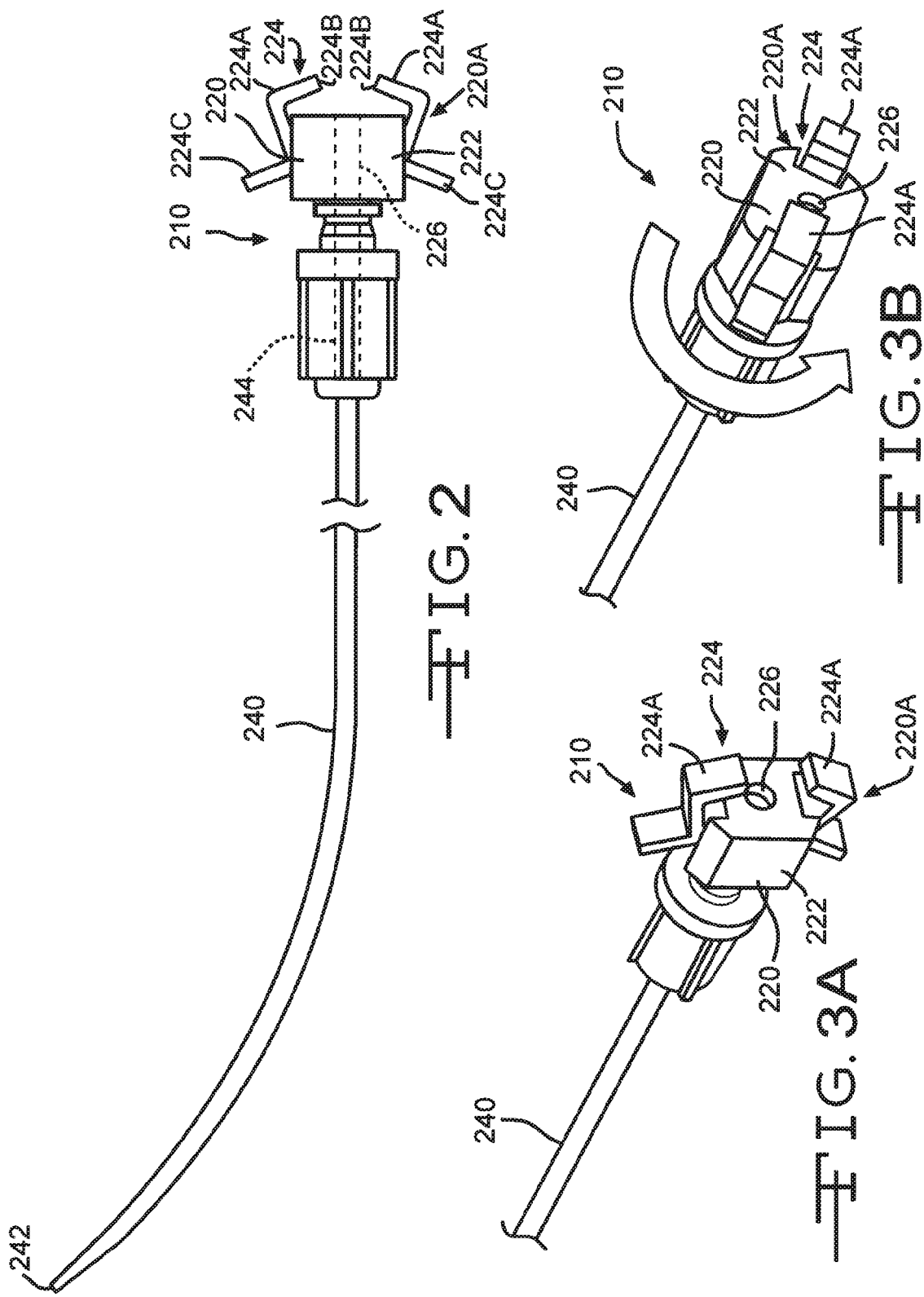

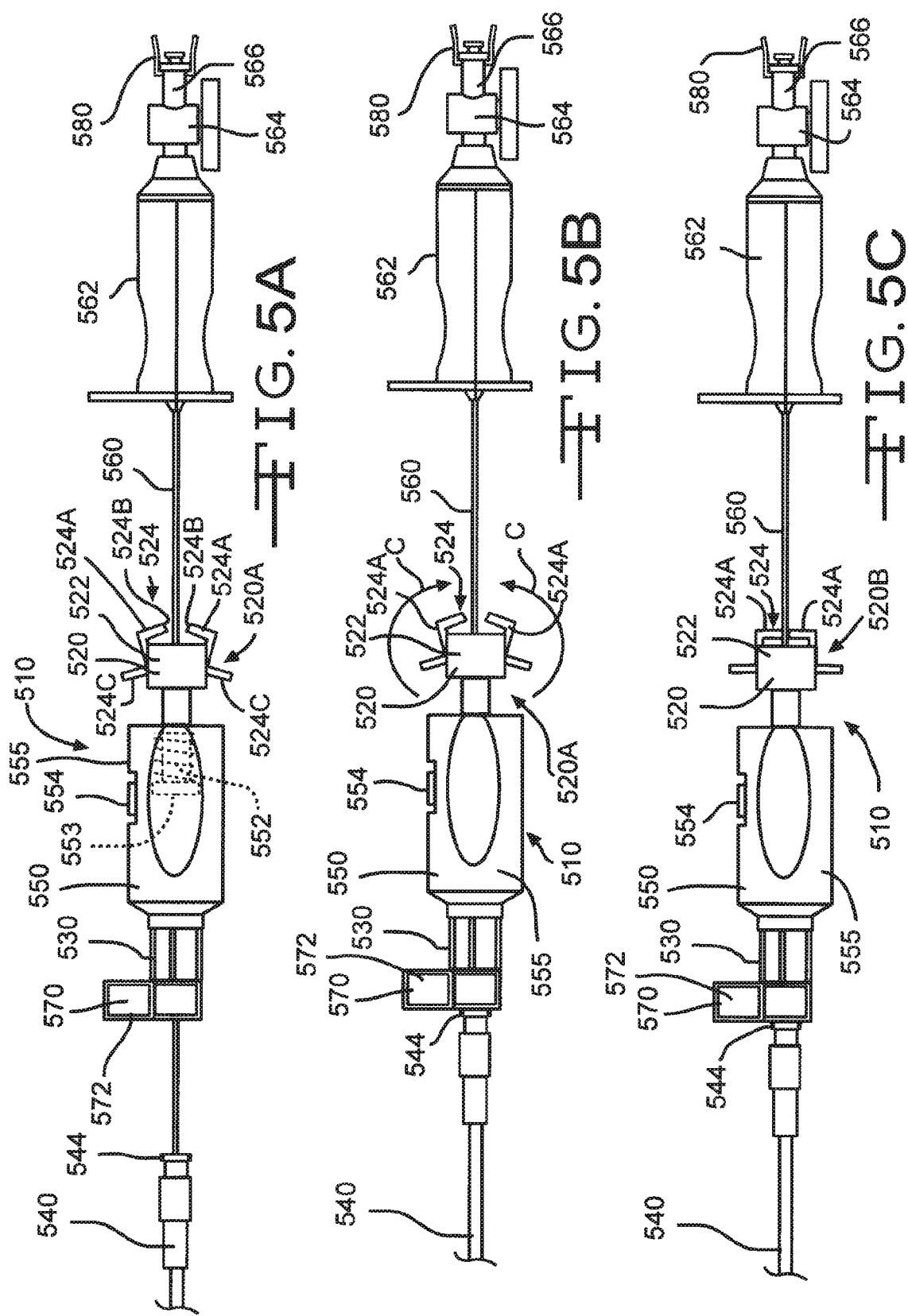

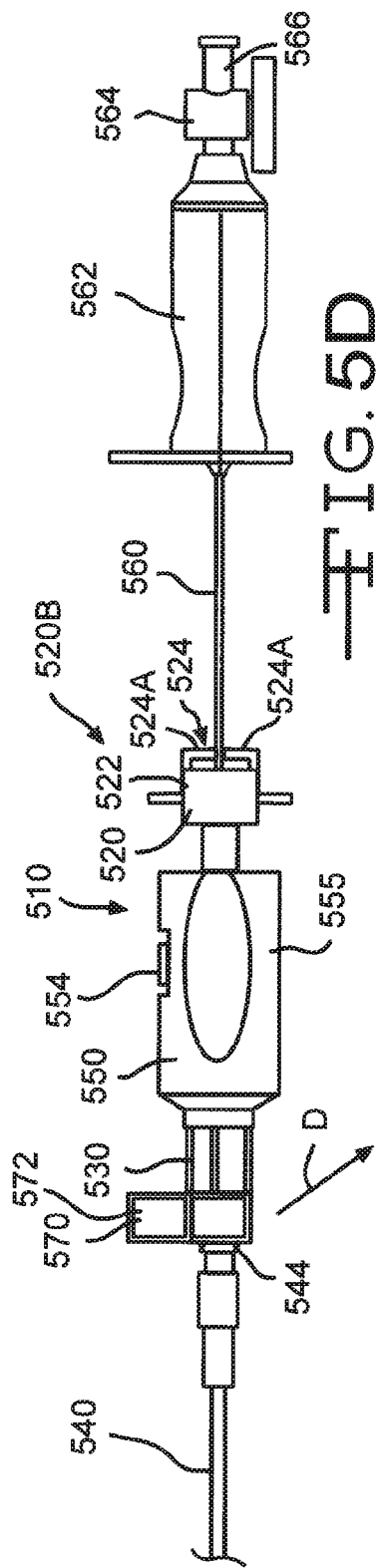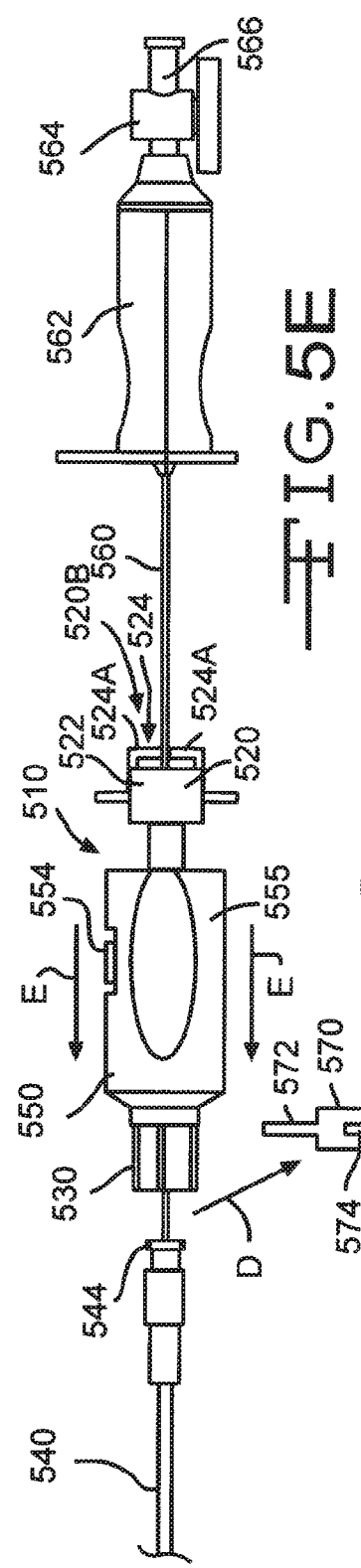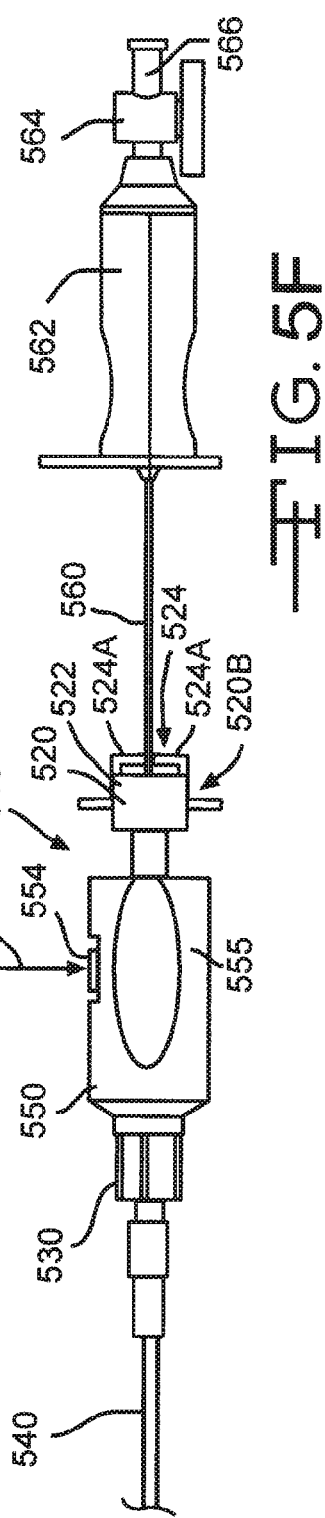

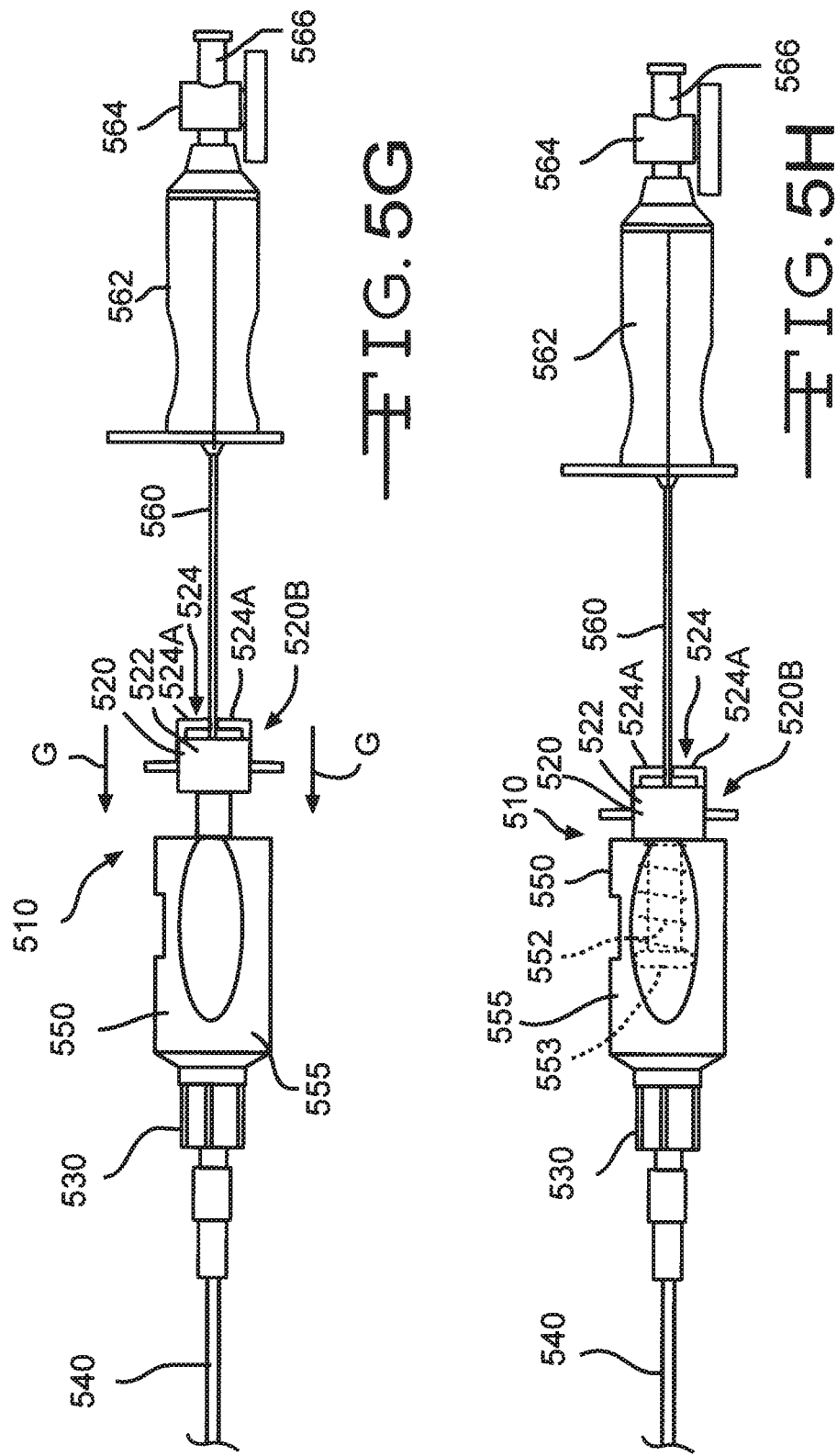

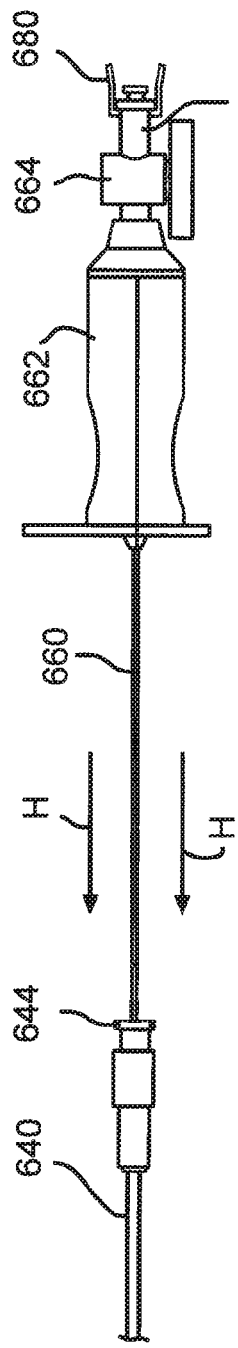
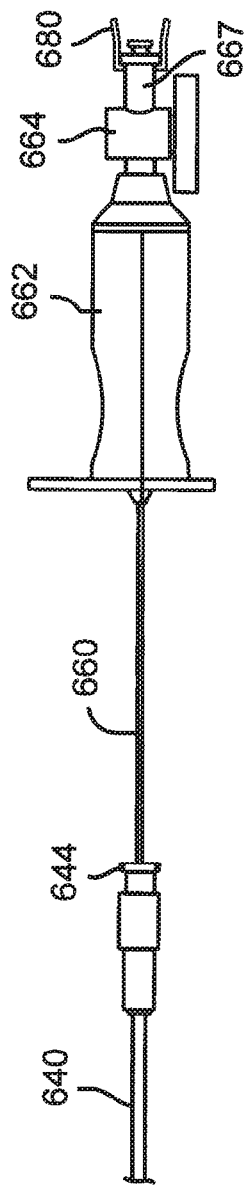
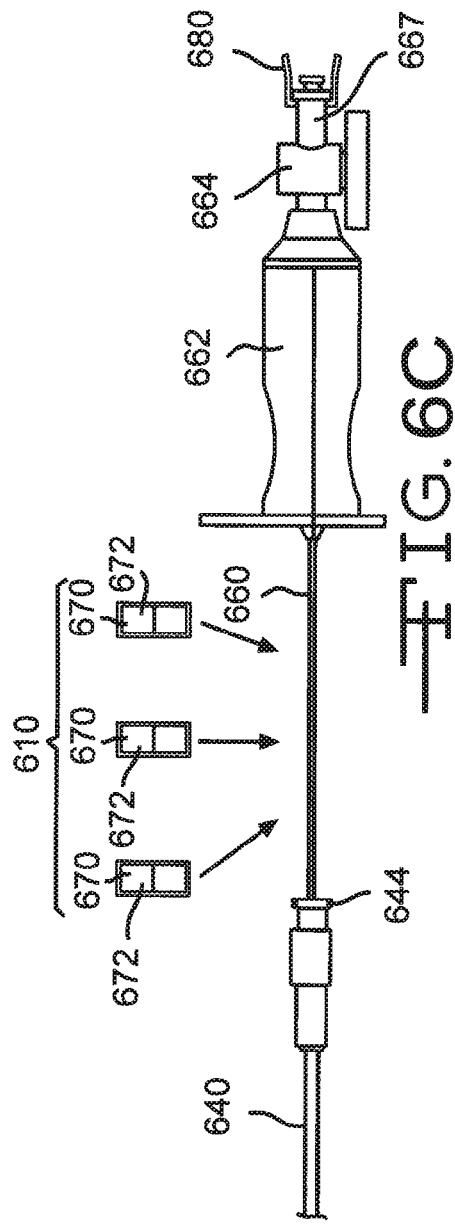
FIG. 6A
FIG. 6B
FIG. 6C

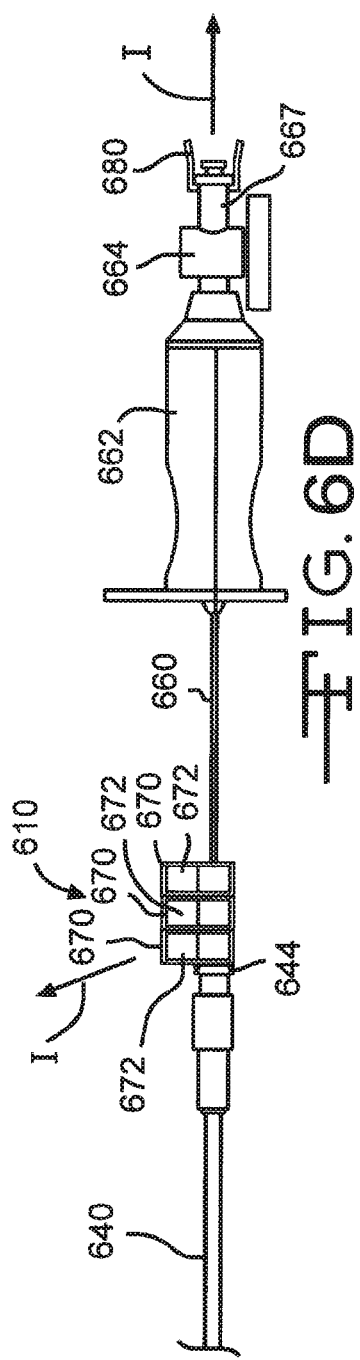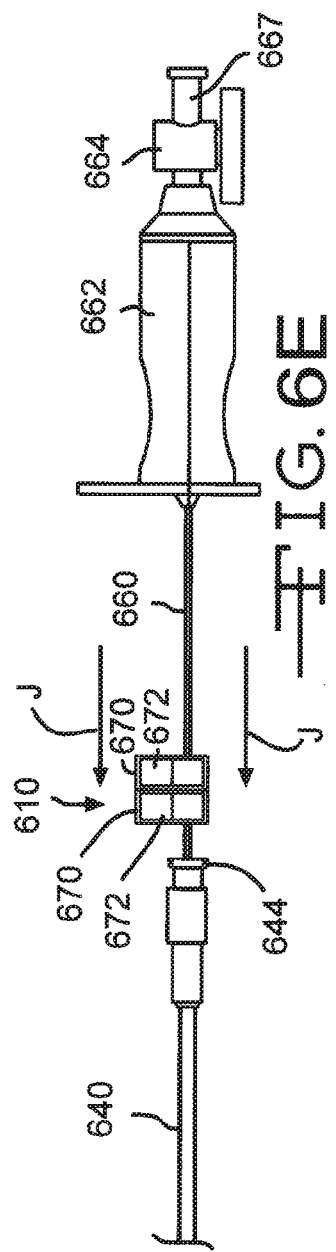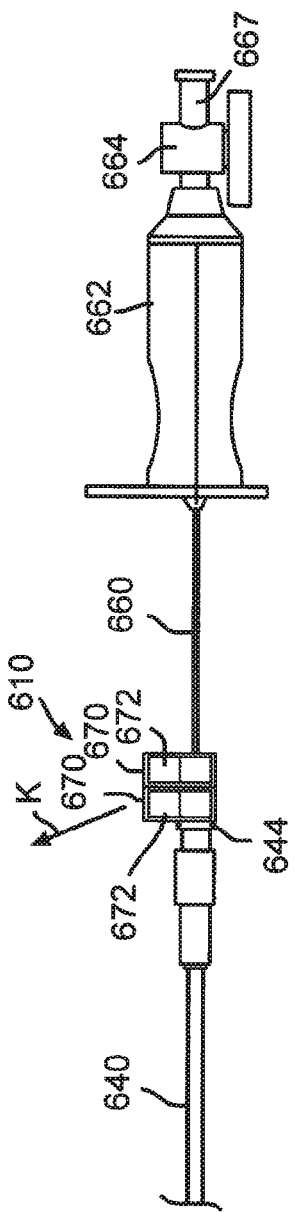

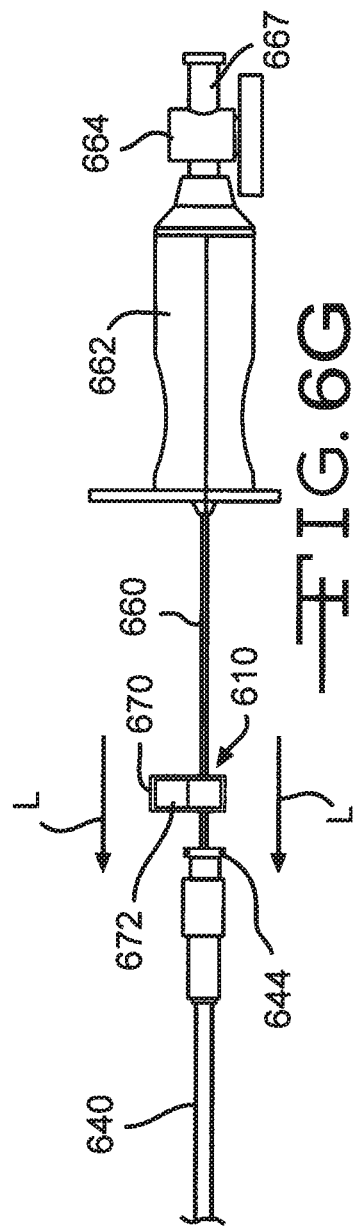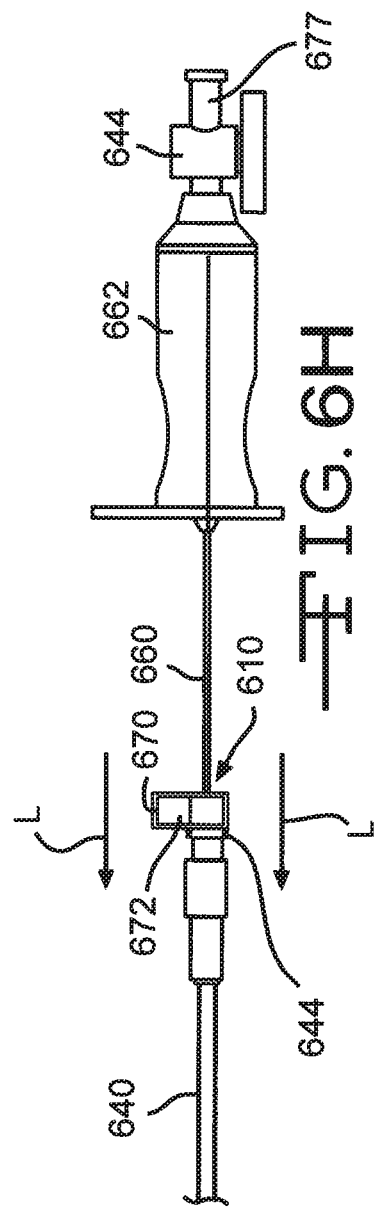

TRANSSEPTAL NEEDLE APPARATUS

CROSS REFERENCE TO RELATED APPLICATIONS

This application claims the benefit of priority to U.S. Provisional Application Ser. No. 61/644,180, filed on May 8, 2012, entitled "TRANSSEPTAL NEEDLE," which is incorporated by reference herein in its entirety.

BACKGROUND

The present invention relates to transseptal catheterization, and more specifically relates to a needle assembly for transseptal catheterization, the needle assembly including an adjustable anchor point for anchoring a dilator with respect to a needle cannula.

The human heart contains four chambers: the right atrium, the right ventricle, the left atrium, and the left ventricle. The right atrium is in fluid contact with the superior vena cava (SVC) and the inferior vena cava (IVC). The right atrium is separated from the right ventricle by the tricuspid valve, while the left atrium is separated from the left ventricle by the mitral valve. The right atrium and left atrium are separated by the interatrial septum, while the right ventricle and left ventricle are separated by the interventricular septum.

There are a multitude of therapeutic and diagnostic procedures in which a catheter is passed within a guide sheath or over a guide wire to access the chambers of the heart. The right atrium can be accessed from the superior vena cava or inferior vena cava. The right ventricle can be accessed from the right atrium. The left ventricle can be accessed from the aorta. The left atrium can be accessed directly from the left ventricle (through the mitral valve); however, such an approach is relatively difficult maneuver due in part to the tortuous path that must be navigated with the catheter. Such a maneuver is problematic for various reasons, including a bleeding risk and a clotting risk to the patient (because it is the arterial side, it has a relatively high pressure, which exacerbates such risks). In addition, this approach may cause arrhythmias. Therefore, another approach for accessing the left atrium was developed. In this approach, a small hole is placed in the interatrial septum, so that the left atrium can be accessed from the right atrium. This hole is typically created by a needle puncture and is referred to as transseptal catheterization.

In the standard transseptal catheterization procedure, three separate tools are involved: a sheath with a sheath hub, a dilator with a dilator hub, and a needle assembly including a cannula, a needle hub and a stylet. The stylet is usually a small, guidewire-like device that is threaded through the needle cannula and attaches to the needle hub proximally. The distal tip of the stylet extends beyond the distal tip of the needle. The distal section of the needle has a shoulder or tapered section that corresponds with an internal taper at the distal tip of the dilator. When the needle is fully inserted into the dilator, the needle shoulder functions as a hard stop that limits the distance that the tip of the needle can exit from the dilator.

The typical transseptal procedure entails numerous steps. First, right femoral vein access is gained via the Seldinger technique. Second, a guidewire is passed through introducer sheath, which was placed in the first step, into the femoral vein and threaded up the IVC to the SVC. Third, a sheath and dilator assembly is maneuvered to the SVC by being passed over the guidewire. Fourth, the guidewire is removed. Fifth, the needle assembly, usually including the stylet, is advanced through the inner lumen of the dilator until the distal tip of the needle (or stylet) is just proximal of the distal tip of the dilator. Sixth, the stylet, if present, is removed, and the needle is advanced until the tip of the needle is just proximal of the distal tip of the dilator. Seventh, the dilator/sheath/needle assembly is pulled caudally until the distal tip of the dilator is just resting on the fossa ovalis, which is a relatively thin area in the interatrial septum. Eighth, the needle is advanced forward through the dilator to puncture the septal wall (fossa ovalis). Ninth, and finally, the sheath and dilator assembly is fed through the septal wall over the needle, thereby gaining access to the left atrium.

One risk associated with transseptal needle use is inadvertent exposure. The sheath/dilator assembly and transseptal needle assembly are usually not interlocking. Thus, the needle assembly can freely translate and rotate within the sheath/dilator assembly. This freedom of movement means that the position of the needle assembly in relation to the sheath/dilator assembly must be manually maintained by the user. In particular, during the needle insertion step and the subsequent navigation of the tip of the sheath/dilator/needle assembly to the fossa ovalis, if the translational position of the needle assembly is not controlled or monitored, there is a risk of inadvertent exposure of the stylet and/or needle tip. The maintenance of needle position in relation to the dilator is especially challenging for inexperienced users. These issues can be exacerbated by the existence of multiple manufacturers of sheaths/dilator assemblies and needle assemblies; each manufacturer can have multiple different lengths of each. Therefore, if a user uses a particular dilator with a non-matched needle length or with a needle from a different manufacturer, for instance, the needle tip or stylet may inadvertently extend from the dilator. Inadvertent exposure can result in damage to the vascular and cardiac walls, which could further result in generation of potentially dangerous emboli.

Moreover, because there can be three or more lengths of sheaths/dilator assemblies/kits that the clinician can use for the procedure and there are different manufacturers of the sheath/dilator kits, each sheath/dilator assembly has a slightly different overall length and handle geometry, each length of sheath/dilator assembly requires a transseptal needle of the same length and/or manufacturer. In order to accommodate this, a hospital has to carry a larger and more varied inventory and the staff has to be sure to pull the correct needle for each procedure.

In the standard transseptal procedure, in order to mitigate this risk, the physician performs a measurement ex vivo to determine the point at which the stylet and/or needle tip is unexposed and just proximal of the dilator tip. To do this, the physician first inserts the needle fully into the dilator so that the stylet and/or needle tip exits the dilator. Next, the physician withdraws the needle proximally so that the stylet and/or needle tip is no longer exposed. At this point, the physician measures how far the needle handle is proximally offset from the dilator hub. Generally, this offset distance is "two-finger-widths" if the stylet is connected to the needle and "one-finger-width" if the stylet has been removed. This is an imprecise and non-standardized measurement that adds an extra step to the procedure. In addition, when the needle is inserted into the dilator and sheath assembly, which has been placed previously in vivo and in the SVC, the physician has to take care that the needle does not advance beyond the offset distance that had been previously measured.

OVERVIEW

This overview is intended to provide an overview of subject matter of the present patent application. It is not intended to provide an exclusive or exhaustive explanation of the invention. The detailed description is included to provide further information about the present patent application.

The present inventors have recognized, among other things, that the subject matter can be used to selectively and adjustably anchor a dilator with respect to a needle cannula in a procedure for puncturing a tissue layer, for instance, puncturing of a septal wall during transseptal catheterization. To better illustrate the apparatuses and methods described herein, a non-limiting list of examples is provided here:

Example 1 can include subject matter that can include an apparatus including a gripping member including a body and a gripping portion attached to the body. The body includes a passage configured to accept a needle cannula within the passage. The gripping member includes an open configuration in which the needle cannula is movable within the passage and a closed configuration in which the gripping portion engages the needle cannula to inhibit movement of the needle cannula within the passage. A coupling member is rotatably attached to the gripping member. The coupling member is configured to selectively couple with a dilator. The coupling member includes a bore fluidly coupled with the passage. The bore is configured to accept the needle cannula within the bore.

In Example 2, the subject matter of Example 1 is optionally configured such that the gripping portion compressively engages the needle cannula in the closed configuration.

In Example 3, the subject matter of any one of Examples 1-2 is optionally configured such that the gripping portion includes a wing movable with respect to the body. The wing is movable between the open configuration and the closed configuration. The wing includes a surface configured to contact the needle cannula in the closed configuration to inhibit movement of the needle cannula within the passage.

In Example 4, the subject matter of any one of Examples 1-3 is optionally configured such that the gripping portion includes at least two wings movable with respect to the body. Each of the wings is movable between the open configuration and the closed configuration. Each of the wings includes a surface configured to contact the needle cannula in the closed configuration to inhibit movement of the needle cannula within the passage.

In Example 5, the subject matter of Example 4 is optionally configured such that two of the at least two wings are diametrically opposed from one another.

In Example 6, the subject matter of any one of Examples 1-5 is optionally configured such that the gripping member includes a Tuohy-Borst valve.

In Example 7, the subject matter of any one of Examples 1-6 optionally includes a puncture member including a first portion attached to the gripping member. A second portion is movable with respect to the first portion, the second portion being attached to the coupling member, wherein, with the gripping member engaged with the needle cannula in the closed configuration and the dilator coupled to the coupling member, movement of the first portion with respect to the second portion moves the needle cannula with respect to the dilator.

In Example 8, the subject matter of Example 7 is optionally configured such that the puncture member includes a potential energy storage member disposed between the first portion and the second portion. An actuator operatively is coupled to the potential energy storage member, wherein triggering of the actuator releases the potential energy storage member to move the first portion with respect to the second portion. With the gripping member engaged with the needle cannula in the closed configuration and the dilator coupled to the coupling member, triggering of the actuator releases the potential energy storage member to move the needle cannula with respect to the dilator.

In Example 9, the subject matter of Example 8 is optionally configured such that the potential energy storage member includes a spring.

In Example 10, the subject matter of any one of Examples 7-9 optionally includes a spacer removably coupled between the first portion and the second portion, wherein, with the spacer coupled between the first portion and the second portion, movement of the first portion with respect to the second portion is inhibited.

Example 11 can include, or can optionally be combined with any one of Examples 1-10 to include subject matter that can include an apparatus including a gripping member including a body and a gripping portion attached to the body. The body includes a passage configured to accept a needle cannula within the passage. The gripping member includes an open configuration in which the needle cannula is movable within the passage and a closed configuration in which the gripping portion engages the needle cannula to inhibit movement of the needle cannula within the passage. A dilator is rotatably attached to the gripping member. The dilator includes a lumen fluidly coupled with the passage. The lumen is configured to accept the needle cannula within the lumen.

In Example 12, the subject matter of Example 11 is optionally configured such that the gripping portion compressively engages the needle cannula in the closed configuration.

In Example 13, the subject matter of any one of Examples 11-12 is optionally configured such that the gripping portion includes a wing movable with respect to the body. The wing is movable between the open configuration and the closed configuration. The wing includes a surface configured to contact the needle cannula in the closed configuration to inhibit movement of the needle cannula within the passage.

In Example 14, the subject matter of any one of Examples 11-13 is optionally configured such that the gripping portion includes at least two wings movable with respect to the body. Each of the wings is movable between the open configuration and the closed configuration. Each of the wings includes a surface configured to contact the needle cannula in the closed configuration to inhibit movement of the needle cannula within the passage.

In Example 15, the subject matter of Example 14 is optionally configured such that two of the at least two wings are diametrically opposed from one another.

In Example 16, the subject matter of any one of Examples 11-15 optionally includes a puncture member including a first portion attached to the gripping member. A second portion is movable with respect to a the first portion, the second portion being attached to the dilator. A potential energy storage member is disposed between the first portion and the second portion. An actuator is operatively coupled to the potential energy storage member, wherein triggering of the actuator releases the potential energy storage member to move the first portion with respect to the second portion, and, in turn, to move the needle cannula with respect to the dilator.

In Example 17, the subject matter of Example 16 is optionally configured such that the potential energy storage member includes a spring.

Example 18 can include, or can optionally be combined with any one of Examples 1-17 to include subject matter that can include an apparatus including a gripping member including a body and a gripping portion attached to the body. The body includes a passage configured to accept a needle cannula within the passage. The gripping member includes an open configuration in which the needle cannula is movable within the passage and a closed configuration in which the gripping portion engages the needle cannula to inhibit movement of the needle cannula within the passage. A puncture member includes a first portion attached to the gripping portion. A second portion is movable with respect to the first portion. A potential energy storage member is disposed between the first portion and the second portion. An actuator is operatively coupled to the potential energy storage member, wherein triggering of the actuator releases the potential energy storage member to move the first portion with respect to the second portion.

In Example 19, the subject matter of Example 18 optionally includes a coupling member rotatably attached to the gripping member. The coupling member is configured to selectively couple with a dilator. The coupling member includes a bore fluidly coupled with the passage. The bore is configured to accept the needle cannula within the bore, wherein, with the gripping member engaged with the needle cannula in the closed configuration and the dilator coupled to the coupling member, triggering of the actuator releases the potential energy storage member to move the needle cannula with respect to the dilator.

In Example 20, the subject matter of any one of Examples 18-19 optionally includes a dilator rotatably attached to the gripping member. The dilator includes a lumen fluidly coupled with the passage. The lumen is configured to accept the needle cannula within the lumen, wherein triggering of the actuator releases the potential energy storage member to move the needle cannula with respect to the dilator.

BRIEF DESCRIPTION OF THE DRAWINGS

FIGS. 1A-1D are side views of an adjustable needle assembly in accordance with at least one example of the invention.

FIG. 2 is a side view of an adjustable needle assembly in accordance with at least one example of the invention.

FIGS. 3A and 3B are perspective views of an adjustable needle assembly in accordance with at least one example of the invention.

FIGS. 5A-5H are side views of an adjustable needle assembly in accordance with at least one example of the invention.

FIGS. 6A-6H are side views of an adjustable needle assembly in accordance with at least one example of the invention.

DETAILED DESCRIPTION

Figure 4A:
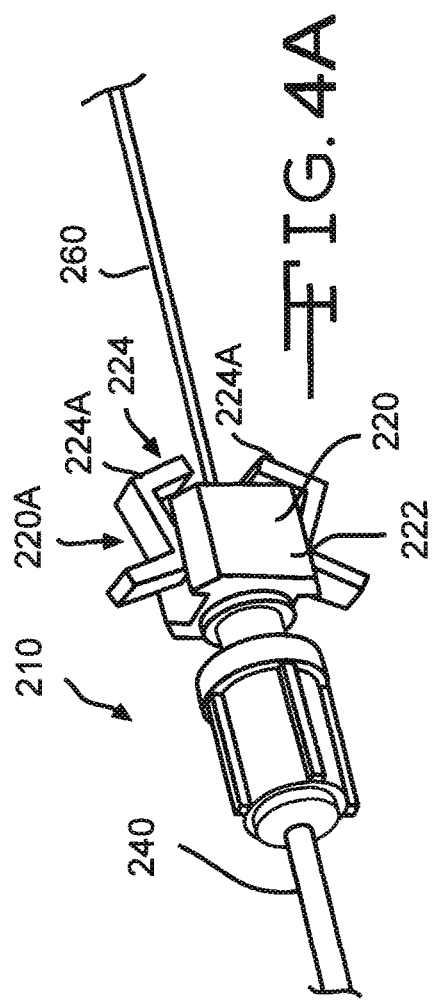
FIGS. 4A-4C are perspective views of an adjustable needle assembly in accordance with at least one example of the invention.

The present patent application relates to apparatuses and methods for adjustably coupling a dilator to a needle cannula. Allowing the dilator to be adjustably coupled to the needle cannula allows variously-sized dilators to be used with variously-sized needle cannulas, thereby lessening, if not eliminating, the need to use a specific size of dilator with a specific size of needle cannula. In some examples, allowing the dilator to be adjustably coupled to the needle cannula allows dilators of various lengths to be used with needle cannulas of various lengths, thereby lessening, if not eliminating, the need to use a specific length of dilator with a specific length of needle cannula. The apparatuses and methods, in some examples, are used in various procedures, including, but not limited to, tissue puncture procedures, interatrial septum puncture procedures, or transseptal catheterization procedures.

The present subject matter provides adjustable needle assembly, sometimes referred to as a "one length fits all" needle assembly, for transseptal catheterization, in some examples, that may be used with different lengths of needle cannulas, dilators, and/or sheaths. The present subject matter includes a locking mechanism to selectively lock a needle cannula at an appropriate length within a dilator (for instance, with a needle tip disposed within the dilator and not extending from a distal tip of the dilator). In some examples, movement of the needle cannula with respect to the dilator is inhibited until a physician or other user is ready to perform the procedure (for instance, a puncture of tissue). The present subject matter can thus reduce the risk of inadvertent exposure of the needle tip before the tip of the dilator/sheath/needle assembly is disposed in the proper location for the particular procedure (for instance, placed on the fossa ovalis). The present subject matter also lessens, if not eliminates, the need for a physician or other user to maintain imprecisely measured spacing of the dilator with respect to the needle cannula in order to maintain the needle tip within the dilator and unexposed until the physician or other user is ready to perform a puncture procedure.

Referring to FIGS. 1A-1D, in some examples, an apparatus or adjustable assembly 110 is configured to selectively engage with another member, such as, but not limited to, a needle cannula 160. In some examples, the adjustable assembly 110 includes a gripping member 120 including a body 122 and a gripping portion 124 attached to the body 122. The body 122, in some examples, includes a passage 126 configured to accept the needle cannula 160 within the passage 126. In some examples, the passage 126 is sized such that the needle cannula 160 fits within and can be relatively easily slidably moved through the passage 126 if otherwise unconstrained. The gripping member 120, in some examples, includes an open configuration 120A (FIGS. 1A, 1B, and 1D) in which the needle cannula 160 is movable within the passage 126. In some examples, the gripping member 120 includes a closed configuration 120B (FIG. 1C) in which the gripping portion 120 engages the needle cannula 160 to inhibit movement of the needle cannula 160 within the passage 126.

In some examples, the gripping member 120 compressively engages the needle cannula 160 in the closed configuration 120B. In some examples, the gripping member 120 includes a Tuohy-Borst valve, which compresses around the needle cannula 160 in the closed configuration with rotation of an outer portion of the Tuohy-Borst valve in a first direction and releases the needle cannula 160 in the open configuration with rotation of the outer portion of the Tuohy-Borst valve in a second direction opposite the first direction.

In some examples, referring now to FIG. 1A, the gripping member 120 includes the gripping portion 124 including a wing 124A movable with respect to the body 122. In some examples, the wing 124A is rotatable with respect to the body 122. In other examples, the wing can be movable in other ways, including, but not limited to, slidable movement. In some examples, the wing 124A is hinged to the body 122. In some examples, the wing 124A is pivotable about a pin coupled to the body 122. In other examples, the wing 124A is movable with respect to the body 122 about a living hinge. In some examples, the wing 124A is movable between the open configuration 120A and the closed configuration 120B. In some examples, the wing 124A is biased toward the closed configuration 120B so that unless the physician or other user is holding onto, touching, or otherwise manipulating the wing 124A, the wing 124A returns to the closed configuration 120B. In various examples, the wing 124A, in the open configuration 120A, allows the needle cannula 160 to move with respect to the wing 124A and, in turn, the adjustable assembly 110 and, in the closed configuration 120B, inhibits movement of the needle cannula 160 with respect to the wing 124A and, in turn, the adjustable assembly 110. In some examples, the wing 124A includes a surface 124B configured to contact the needle cannula 160 in the closed configuration 120B to inhibit movement of the needle cannula 160 within the passage 126. The surface 124B, in various examples, frictionally engages the needle cannula 160 in the closed configuration 120B to inhibit movement of the needle cannula 160 with respect to the surface 124B. In some examples, the surface 124B includes a grip pattern to enhance frictional engagement with the needle cannula 160. In some examples, the surface 124B includes or is formed from a material configured to enhance frictional engagement with the needle cannula 160. For instance, in some examples, the surface 124B can include a rubber or rubber-like material. In some examples, the wing 124A includes a tab 124C or other feature extending from the wing 124A to allow the physician or other user to manipulate the wing 124A between the open configuration 120A and the closed configuration 120B.

In some examples, the gripping portion 124 includes at least two wings 124A movable with respect to the body 122. In some examples, each of the wings 124A is movable between the open configuration 120A and the closed configuration 120B. Each of the wings 124A, in some examples, includes a surface 124B configured to contact the needle cannula 160 in the closed configuration 120B to inhibit movement of the needle cannula 160 within the passage 126. In some examples, two of the at least two wings 124A are diametrically opposed from one another. In some examples, the gripping portion 124 includes more than two wings 124A. In some examples, the wings 124A are evenly spaced from one another around the passage 126. In various examples, the wings 124A are configured to allow the needle cannula 160 to be essentially pinched in between the surfaces 124B of the wings 124A to allow for frictional engagement of the needle cannula 160 by the wings 124A in the closed configuration 120B to inhibit the adjustable assembly 110 from moving with respect to the needle cannula 160.

Referring again to FIGS. 1A-1D, in some examples, the adjustable assembly 110 includes a coupling member 130 attached to the gripping member 120. In some examples, the coupling member 130 is rotatably attached to the gripping member 120. In some examples, the coupling member 130 is configured to selectively couple with another member, such as, but not limited to, a dilator 140. In some examples, the coupling member 130 includes a Luer connector. In further examples, the coupling member 130 includes a male Luer portion configured to removably couple to a female Luer portion, for instance, a female Luer portion 144 of the dilator 140 (FIG. 1B). In other examples, the coupling member 130 is a type of connector other than a Luer connector, such as, but not limited to, a threaded coupling (other than a Luer connector), a snap fitting, a collet fitting, a magnetic coupling, or the like, for instance. In some examples, the coupling member 130 includes a bore 132 fluidly coupled with the passage 126 of the gripping member 120. In some examples, the bore 132 is configured to accept the needle cannula 160 within the bore 132. In some examples, the bore 132 and the passage 126 are coaxially disposed within the adjustable assembly 110. In various examples, the passage 126 and the bore 132 are sized and situated within the adjustable assembly 110 to allow the needle cannula 160 to pass through the adjustable assembly 110, such that the adjustable assembly 110 with the gripping member 120 in the open configuration 120A can be located at a desired location along the needle cannula 160 and then engaged to the needle cannula 160 at that desired location with the gripping member 120 in the closed configuration 120B.

Figure 8A:
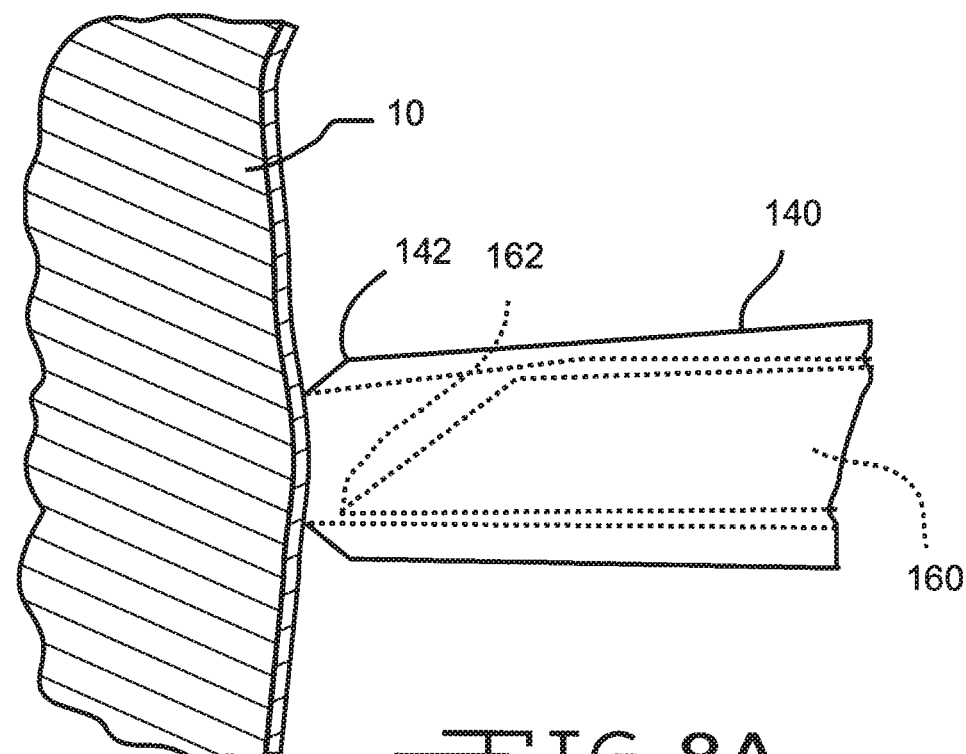
FIGS. 8A and 8B are side views of a needle cannula retracted within a dilator and advanced out of the dilator, respectively.

Referring now to FIGS. 1A-1D, 8A, and 8B, in operation, in some examples, the adjustable assembly 110 can be used to locate and retain the needle cannula 160 in a desired relationship with respect to the dilator 140. For instance, referring briefly to FIG. 8A, in some examples, it can be desirable to position the needle cannula 160 within the dilator 140 such that a needle tip 162 is disposed at or just proximal to a dilator tip 142. In further examples, it can be desirable to maintain this position of the needle tip 162 within the dilator 140, for instance, while positioning the needle cannula 160 and dilator 140 within the patient until the dilator tip 142 is positioned proximate or abutting a tissue layer 10 that is desired to be punctured. In this way, the needle tip 162 can be guarded so as to lessen the likelihood of inadvertently exposing the patient to the needle tip 162. In some examples, referring to FIG. 1A, the gripping member 120 is held in the open configuration 120A and the adjustable assembly 110 is placed on the needle cannula 160. The dilator 140 can also be placed over the needle cannula 160. Referring to FIG. 1B, the dilator 140, in some examples, can then be coupled to the adjustable assembly 110, for instance by engaging the female Luer portion 144 of the dilator 140 to the coupling member 130 of the adjustable assembly 110. In other examples, the dilator 140 can be coupled to the adjustable assembly 110 prior to placement of the adjustable assembly 110 onto the needle cannula 160 and then the dilator 140 coupled to the adjustment assembly 110 can be placed onto the needle cannula 160 together. In some examples, with the dilator 140 coupled to the adjustable assembly 110 and the dilator 140 and the adjustable assembly 110 on the needle cannula 160, the gripping member 120 is maintained in the open configuration 120A to slidably locate the adjustment assembly 110 in the desired location along the needle cannula 160. For instance, the desired location, in some examples, is the point along the needle cannula 160 at which the needle tip 162 is positioned at or just proximal to the dilator tip 142 (FIG. 8A). In other examples, other positions of the needle tip 162 with respect to the dilator tip 142 can be desirable.

Once the desired location of the adjustable assembly 110 is reached, referring to FIG. 1C, in some examples, the physician or other user can place the gripping member 120 in the closed configuration 120B (for instance, by releasing the one or more tabs 124O of the one or more wings 124A to allow the one or more wings 124A to return to the closed configuration 120B or by rotating the outer portion of the Tuohy-Borst valve in a tightening direction) to grip or otherwise compressively or frictionally engage the needle cannula 160 and inhibit movement of the adjustment assembly 110 and, in turn, the dilator 140 with respect to the needle cannula 160. In some examples, positioning the adjustment assembly 110 in this way engages the needle cannula 160 to inhibit the needle tip 162 from inadvertently moving distally from the dilator tip 142. The needle cannula 160 and the dilator 140 can then be placed in the desired location within the patient, for instance, with the dilator tip 142 proximate or abutting the tissue layer 10 desired to be punctured (FIG. 8A). In some examples, with the coupling member 130 rotatable with respect to the gripping member 120, rotation of the needle cannula 160 with respect to the dilator 140 can be accomplished, for instance, to facilitate maneuvering of the dilator 140 and needle cannula 160 to the desired location within the patient.

Figure 8B:
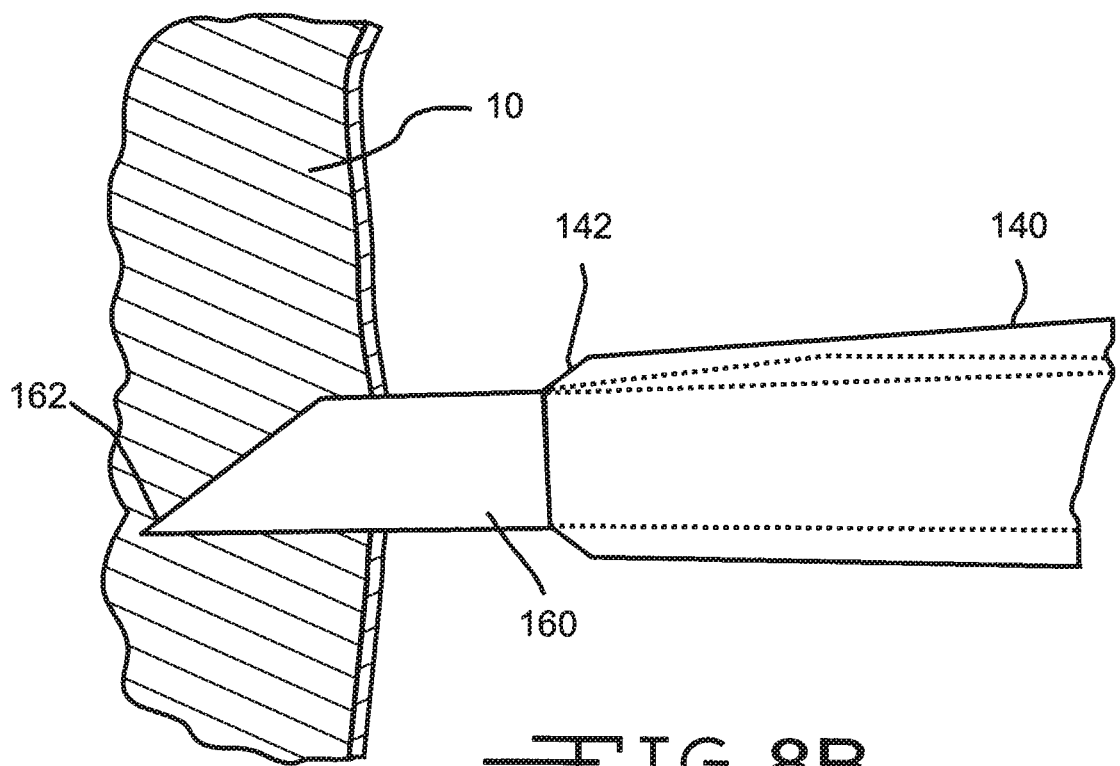

Referring to FIGS. 1D and 8B, in some examples, with the dilator 140 and needle cannula 160 in the desired position for puncturing, the gripping member 120 is placed in the open configuration 120A and the needle cannula 160 is advanced distally along arrow A with respect to the adjustment assembly 110 and the dilator 140 to extend the needle tip 162 distally from the dilator tip 142 and puncture the tissue layer 10.

Referring now to FIGS. 2-4C, in some examples, an adjustable assembly 210 is similar to the adjustable assembly 110 described herein. For instance, in some examples, the adjustable assembly 210 includes a gripping member 220 including a gripping portion 224 attached to a body 222. Similar to the gripping member 120 described herein, in various examples, the gripping member 220 can include the gripping portion 224 including one or more wings 224A, a Tuohy-Borst valve, or the like. In some examples, the adjustable assembly 210 differs from the adjustable assembly 110 in that, rather than having a dilator 140 removably couplable with the adjustment assembly 110, the adjustable assembly 210 includes a dilator 240 attached to the gripping member 220 in a manner that is not intended to be removed. In some examples, the dilator 240 is integrally attached to the gripping member 220. In some examples, the dilator 240 is rotatably attached to the gripping member 220 so that the gripping member 220 can rotate with respect to the dilator 240. Although the gripping member 220 is shown rotating counterclockwise with respect to the dilator 240 between FIGS. 3A and 3B, in some examples, it is contemplated that the gripping member 220 can rotate either counterclockwise or clockwise with respect to the dilator 240. In some examples, the dilator 240 includes a lumen 244 fluidly coupled with a passage 226 of the gripping member 220. In some examples, the passage 226 of the gripping member 220 is generally similar to the passage 126 of the gripping member 120 described herein. In some examples, the lumen 244 is configured to accept a needle cannula 260 (FIGS. 4A-4C) within the lumen 240. In some examples, the adjustable assembly 210 is configured to accept the needle cannula 260 within the passage 226 and lumen 244 to allow the adjustable assembly 210 to be selectively slidably movable along the needle cannula 260 similar to the selectively slidably movement of the adjustable assembly 110 along the needle cannula 160 described herein.

Figure 4C:
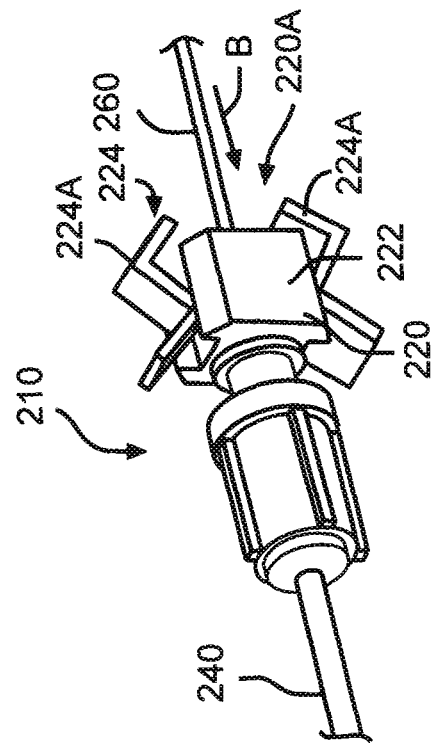
Figure 4B:
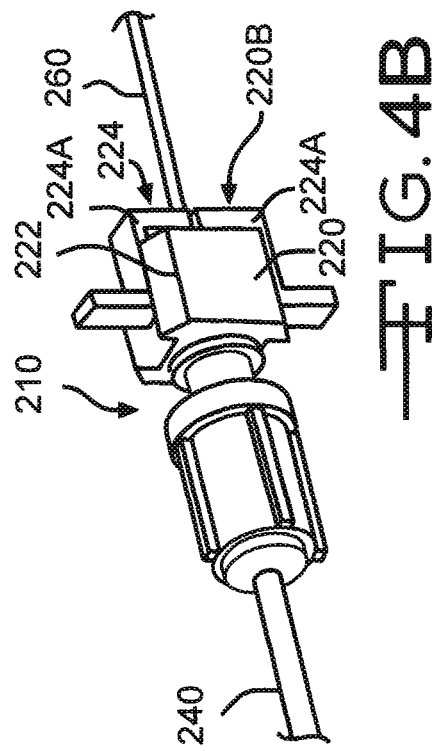

Referring to FIGS. 4A-4C, in operation, in some examples, the adjustable assembly 210 can be used to locate and retain the needle cannula 260 in a desired relationship with respect to the dilator 240. For instance, in a manner similar to that described herein and shown in FIG. 8A, in some examples, it can be desirable to position the needle cannula 260 within the dilator 240 such that a needle tip is disposed at or just proximal to a dilator tip 242. In this way, the needle tip can be guarded so as to lessen the likelihood of inadvertently exposing the patient to the needle tip. In some examples, referring to FIG. 4A, the gripping member 220 is held in an open configuration 220A and the adjustable assembly 210 is placed on the needle cannula 260. In some examples, the gripping member 220 is maintained in the open configuration 220A to slidably locate the adjustment assembly 210 in the desired location along the needle cannula 260. For instance, the desired location, in some examples, is the point along the needle cannula 260 at which the needle tip is positioned at or just proximal to the dilator tip 242 (in a manner similar to that which is shown in FIG. 8A). In other examples, other positions of the needle tip with respect to the dilator tip 242 can be desirable.

Once the desired location of the adjustable assembly 210 is reached, referring to FIG. 4B, in some examples, the physician or other user can place the gripping member 220 in a closed configuration 220B (for instance, by releasing one or more tabs 224C of the one or more wings 224A to allow the one or more wings 224A to return to the closed configuration 220B with one or more surfaces 224B of the one or more wings 224A in frictional engagement with the needle cannula 260 or by rotating the outer portion of the Tuohy-Borst valve in a tightening direction) to grip or otherwise compressively or frictionally engage the needle cannula 260 and inhibit movement of the adjustment assembly 210 and, specifically, the dilator tip 242 with respect to the needle cannula 260. In some examples, positioning the adjustment assembly 110 in this way engages the needle cannula 260 to inhibit the needle tip from inadvertently moving distally from the dilator tip 242. The needle cannula 260 and the adjustable assembly 210 can then be placed in the desired location within the patient, for instance, with the dilator tip 242 proximate or abutting the tissue layer desired to be punctured (in a manner similar to that which is shown in FIG. 8A). In some examples, with the dilator 240 rotatable with respect to the gripping member 220, rotation of the needle cannula 260 with respect to the dilator 240 can be accomplished, for instance, to facilitate maneuvering of the dilator 240 and the needle cannula 260 to the desired location within the patient.

Referring to FIG. 4C, in some examples, with the dilator 240 and the needle cannula 260 in the desired position for puncturing, the gripping member 220 is placed in the open configuration 220A and the needle cannula 260 is advanced distally along arrow B with respect to the adjustment assembly 210 to extend the needle tip distally from the dilator tip 242 and puncture the tissue layer.

Referring to FIGS. 5A-5H, in some examples, an adjustable assembly 510 is similar to the adjustable assembly 110 described herein. For instance, in some examples, the adjustable assembly 510 includes a gripping member 520 including a gripping portion 524 attached to a body 522. In some examples, the gripping member 520 includes a passage similar to the passage 126 described herein. Similar to the gripping member 120 described herein, in various examples, the gripping member 520 can include the gripping portion 524 including one or more wings 524A, a Tuohy-Borst valve, or the like. In some examples, the gripping member 520 includes an open configuration 520A and a closed configuration 520B similar to the open configuration 120A and the closed configuration 120B described herein with respect to the adjustable assembly 110.

In some examples, the adjustable assembly 510 includes a coupling member 530. In some examples, the coupling member 530 is rotatably attached with respect to the gripping member 520. In some examples, the coupling member 530 is configured to selectively couple with another member, such as, but not limited to, a dilator 540. In some examples, the coupling member 530 includes a Luer connector. In further examples, the coupling member 530 includes a male Luer portion configured to removably couple to a female Luer portion, for instance, a female Luer portion 544 of the dilator 540 (FIG. 5A). In other examples, the coupling member 530 is a type of connector other than a Luer connector, such as, but not limited to, a threaded coupling (other than a Luer connector), a snap fitting, a collet fitting, a magnetic coupling, or the like, for instance. In some examples, the coupling member 530 includes a bore, similar to the bore 132 of the adjustable assembly 110 described herein, fluidly coupled with the passage of the gripping member 520.

In some examples, the adjustable assembly 510 is configured to adjustably anchor the adjustable assembly 510 and, in turn, the dilator 540 with respect to a needle cannula 560. In some examples, the needle cannula 560 includes a handle 562 engaged at a proximal end of the needle cannula 562 to facilitate the physician or other user in handling or maneuvering the needle cannula 560. In some examples, the handle includes a port 566 fluidly coupled to a lumen of the needle cannula 560 to which to attach a syringe (for injecting contrast material, for instance), a positive pressure source, a negative pressure source, or the like. In some examples, the port 566 includes a stopcock 564 or other coupling assembly configured to selectively open or close the port 566. In some examples, the port 566 is configured to accept a stylet 580 in order to insert the stylet 580 within the lumen of the needle cannula 560. Although shown used with the needle cannula 560 and the handle 562 described herein, it is contemplated that the adjustable assembly 510 can be used with another needle cannula or another apparatus or assembly.

In some examples, the adjustable assembly 510 differs from the adjustable assembly 110 in that the adjustable assembly 510 includes a puncture member 550. In some examples, the puncture member 550 is configured to selectively allow for at least partially automated puncturing of a tissue layer with a needle tip of the needle cannula 560 (in a manner similar to that which is shown in FIG. 8B). The puncture member 550, in some examples, is coupled to the gripping member 520 on one side and the coupling member 530 on the other side. In some examples, the coupling member 530 is rotatably attached to the puncture member 550. In some examples, the puncture member 550 fluidly couples the passage of the gripping member 520 and the bore of the coupling member 530 to allow the needle cannula 560 to extend through the adjustable assembly 510. In some examples, the puncture member 550 includes a first portion 553 attached to the gripping member 520. The puncture member 550, in some examples, includes a second portion 555 movable with respect to the first portion 553. In some examples, the first portion includes a shaft-like portion extending from the gripping member 520 and into the second portion 555. In some examples, the first portion 553 and second portion 555 form a piston-like assembly. In some examples, the second portion 555 is attached to the coupling member 530. In this way, in some examples, with the gripping member 520 engaged with the needle cannula 560 in the closed configuration 520B and the dilator 540 coupled to the coupling member 530, movement of the first portion 553 with respect to the second portion 555 moves the needle cannula 560 with respect to the dilator 540. In this way, in some examples, a puncture of a tissue layer can be performed (similar to that which is shown in FIG. 8B) by moving the first portion 553 with respect to the second portion 555. In some examples, during the puncturing of the tissue layer, the second portion 555 and, in turn, the dilator 540, is substantially held stationary with respect to the patient and the first portion 553 and, in turn, the needle cannula 560 is advanced distally with respect to the dilator 540 to allow the needle tip to extend from the dilator and puncture the desired tissue layer. In other examples, the first portion 553 and, in turn, the needle cannula 560, can be substantially held stationary with respect to the patient and the second portion 555 and, in turn, the dilator 540 is advanced proximally with respect to the needle cannula 560.

In some examples, the puncture member 550 includes a potential energy storage member 552 disposed between the first portion 553 and the second portion 555. In some examples, the potential energy storage member 552 includes a spring. In other examples, the potential energy storage member 552 can include a compressed air source, opposing magnets, or the like. In some examples, an actuator 554 is operatively coupled to the potential energy storage member 552, wherein triggering of the actuator 554 releases the potential energy storage member 552 to move the first portion 553 with respect to the second portion 555. In some examples, the actuator 554 includes a button. In other examples, the actuator can take other forms, such as, but not limited to a knob, a dial, a slider, a toggle switch or other switch, or the like. In some examples, prior to actuation of the actuator 554, a stop is in place to inhibit the potential energy storage member 552 from being released and to maintain the first portion 553 from moving with respect to the second portion 555 (FIG. 5A). The actuator 554, in some examples, when pushed or otherwise actuated, moves the stop and releases the first portion 553 and the potential energy storage member 552 to allow movement of the first portion 553 with respect to the second portion 555 (FIG. 5H). In some examples, with the gripping member 520 engaged with the needle cannula 560 in the closed configuration 520B and the dilator 540 coupled to the coupling member 530, triggering of the actuator 554 releases the potential energy storage member 552 to move the needle cannula 560 with respect to the dilator 540.

In some examples, the adjustable assembly 510 differs from the adjustable assembly 110 in that the adjustable assembly 510 includes a spacer 570. In some examples, the spacer 570 can be removably disposed on the needle cannula 560 between the dilator 540 and the coupling member 530. In some examples, the dilator 540 can be coupled to the spacer 570, for instance, using the female Luer portion 544 of the dilator 540 to mate with a corresponding male Luer portion of the spacer 570. In other examples, the dilator 540 abuts the spacer 570 without threaded or other engagement. Referring briefly to FIG. 5E, the spacer 570, in some examples, includes a slot 574 configured to selectively frictionally engage with the needle cannula 560. In this way, in some examples, the spacer 570 can be selectively removed from the needle cannula 560 at which point the physician or other user desires to do so. In some examples, the spacer 570 includes a tab 572 or other feature to facilitate grasping of the spacer 570 by the physician or other user, for instance, during removal of the spacer 570 from the needle cannula 560. In some examples, the spacer 570 can be used to position dilator 540 with respect to the needle cannula 560, for instance, to maintain a stylet tip of the stylet 580 (extending distally from the needle tip of the needle cannula 560) within the dilator 540. In this way, in some examples, the stylet tip can be shielded to lessen the likelihood of inadvertent exposure of the patient to the stylet tip. In some examples, with removal of the stylet 580 from within the needle cannula 560, the spacer 570 can be removed from engagement with the needle cannula 560 and the dilator 540 can be coupled to the coupling member 530 to position the needle tip of the needle cannula 560 proximate the dilator tip of the dilator 540 (similar to that which is shown in FIG. 8A).

Referring to FIGS. 5A-5H, in operation, in some examples, the adjustable assembly 510 can be used to locate and retain the needle cannula 560 in a desired relationship with respect to the dilator 540. For instance, in a manner similar to that described herein and shown in FIG. 8A, in some examples, it can be desirable to position the needle cannula 560 within the dilator 540 such that the stylet tip or the needle tip is disposed at or just proximal to the dilator tip. In this way, the stylet tip or the needle tip can be guarded so as to lessen the likelihood of inadvertently exposing the patient to the stylet tip or the needle tip. In some examples, referring to FIG. 5A, the gripping member 520 is held in the open configuration 520A and the adjustable assembly 510 is placed on the needle cannula 560. In some examples, the spacer 570 is initially placed on the needle cannula 560, as well. The dilator 540, in some examples, can also be placed on the needle cannula 560. In some examples, the gripping member 520 is maintained in the open configuration 520A to slidably locate the adjustment assembly 510 in the desired location along the needle cannula 560. For instance, the desired location, in some examples, is the point along the needle cannula 560 at which the stylet tip is positioned at or just proximal to the dilator tip. In other examples, other positions of the stylet tip with respect to the dilator tip can be desirable. Referring to FIG. 5B, the adjustable assembly 510, the spacer 570, and the dilator 540 can be lined up along the needle cannula 560 and abutted or coupled with one another in order to determine a desired location of the adjustable assembly 510.

Once the desired location of the adjustable assembly 510 is reached, referring to FIG. 5C, in some examples, the physician or other user can place the gripping member 520 in the closed configuration 520B (for instance, by releasing one or more tabs 524C of the one or more wings 524A to allow the one or more wings 524A to return to the closed configuration 520B with one or more surfaces 524B of the one or more wings 524A in frictional engagement with the needle cannula 560 or by rotating the outer portion of the Tuohy-Borst valve in a tightening direction) to grip or otherwise compressively or frictionally engage the needle cannula 560 and inhibit movement of the adjustment assembly 510 and, in turn, the dilator tip of the dilator 540 with respect to the stylet tip and the needle cannula 560. In some examples, positioning the adjustment assembly 510 in this way engages the needle cannula 560 to inhibit the stylet tip of the stylet 580 disposed within the lumen of the needle cannula 560 from inadvertently moving distally from the dilator tip. Referring to FIG. 5D, in some examples, once the stylet 580 is no longer needed for the procedure, the stylet 580 can be removed from within the needle cannula 560, for instance, by pulling the stylet 580 proximally out of the port 566. Once the stylet 580 is removed, in some examples, the spacer 570 can be removed along arrow D. With the spacer 570 removed, in some examples, the adjustable assembly 510 and the needle cannula 560 can be advanced distally along arrows E, as shown in FIG. 5E. In some examples, the spacer 570 is sized such that it maintains the stylet tip disposed within the dilator 540, and, with the removal of the spacer 570, distally advancing the needle cannula 560 and adjustable assembly 510 to close the gap left by the spacer 570 and abutting or coupling the coupling member 530 to the dilator 540 places the needle tip of the needle cannula 560 at or just proximal to the dilator tip.

The needle cannula 560 and the dilator 540 can then be placed in the desired location within the patient, for instance, with the dilator tip proximate or abutting the tissue layer desired to be punctured (in a manner similar to that which is shown in FIG. 8A). In some examples, with the dilator 540 rotatable with respect to the puncture member 550, rotation of the needle cannula 560 with respect to the dilator 540 can be accomplished, for instance, to facilitate maneuvering of the dilator 540 and the needle cannula 560 to the desired location within the patient. Referring to FIG. 5F, in some examples, with the dilator 540 and the needle cannula 560 in the desired position for puncturing, the actuator 554 can be triggered, for instance, by pushing the actuator along arrow F. In some examples, triggering the actuator 554 releases the first portion 553 and the potential energy storage member 552 to allow the first portion 553 to move along arrows G, as shown in FIG. 5G, with respect to the second portion 555. In some examples, referring to FIG. 5H, unconstraining the first portion 553 by triggering the actuator 554 releases the potential energy storage member 552 (for instance, allows extension of a compressed spring) to move the first portion 553 with respect to the second portion 555. In some examples, with the dilator 540 coupled to the coupling member 530, which is attached to the second portion 555, and the needle cannula 560 frictionally engaged with the gripping member 520 in the closed configuration 520B, triggering of the actuator 554 distally advances the first portion 553 and, in turn, the gripping member 520 and needle cannula 560, with respect to the second portion 555 and, in turn, the coupling member 530 and the dilator 540 to extend the needle tip distally from the dilator tip and puncture the tissue layer (in a manner similar to that which is shown in FIG. 8B). In this way, in some examples, the adjustable assembly 510 allows for at least partially automated puncturing of the tissue layer.

Referring to FIGS. 6A-6H, in some examples, an adjustable assembly 610 can be used, for instance, to position a stylet tip of a stylet 680 or a needle tip of a needle assembly 660 with respect to a dilator 640. In other examples, the adjustable assembly 610 can be used to position other assemblies with respect to one another. In some examples, the adjustable assembly 610 is configured to adjustably anchor the adjustable assembly 610 and, in turn, the dilator 640 with respect to the needle cannula 660. In some examples, the needle cannula 660 includes a handle 662 engaged at a proximal end of the needle cannula 660 to facilitate the physician or other user in handling or maneuvering the needle cannula 660. In some examples, the handle includes a port 667 fluidly coupled to a lumen of the needle cannula 660 to which to attach a syringe (for injecting contrast material, for instance), a positive pressure source, a negative pressure source, or the like. In some examples, the port 667 includes a stopcock 664 or other coupling assembly configured to selectively open or close the port 667. In some examples, the port 667 is configured to accept the stylet 680 in order to insert the stylet 680 within the lumen of the needle cannula 660. Although shown used with the needle cannula 660 and the handle 662 described herein, it is contemplated that the adjustable assembly 610 can be used with another needle cannula or another apparatus or assembly.

In some examples, the adjustable assembly 610 includes one or more spacers 670. In some examples, the one or more spacers 670 can be removably disposed on the needle cannula 660 to position the needle cannula 660 with respect to the dilator 640. In some examples, the dilator 640 can be coupled to at least one of the one or more spacers 670, for instance, using a female Luer portion 644 of the dilator 640 to mate with a corresponding male Luer portion of at least one of the spacers 670. In other examples, the dilator 640 abuts the at least one of the spacers 670 without threaded or other engagement. The one or more spacers 670, in some examples, include a slot (similar to the slot 574 of the spacer 570 described herein) configured to selectively frictionally engage with the needle cannula 660. In this way, in some examples, the one or more spacers 670 can be selectively removed from the needle cannula 660 at which point the physician or other user desires to do so. In some examples, the one or more spacers 670 each include a tab 672 or other feature to facilitate grasping of the spacer 670 by the physician or other user, for instance, during removal of the spacer 670 from the needle cannula 660. In some examples, the one or more spacers 670 can be used to position the needle cannula 660 with respect to the dilator 640, for instance, to maintain the stylet tip of the stylet 680 (extending distally from the needle tip of the needle cannula 660) within the dilator 640 or to maintain the needle tip of the needle cannula 660 within the dilator 640. In this way, in some examples, the stylet tip or the needle tip can be shielded to lessen the likelihood of inadvertent exposure of the patient to the stylet tip or needle tip. In some examples, the spacers 670 (if more than one spacer 670 are used) can interlock with or otherwise attach to one another. In further examples, the spacers 670 can interlock such that the spacers 670 can only be removed from the needle cannula 660 in a particular order.

In the examples described herein, the adjustable assembly 610 includes three spacers 670. It is contemplated, however, that in other examples, more or fewer than three spacers 670 can be used to accomplish one or more positioning of the dilator 640 with respect to the needle cannula 660.

Referring still to FIGS. 6A-6H, in operation, in some examples, the adjustable assembly 610 can be used to locate and retain the needle cannula 660 in a desired relationship with respect to the dilator 640. For instance, in a manner similar to that described herein and shown in FIG. 8A, in some examples, it can be desirable to position the needle cannula 660 within the dilator 640 such that the stylet tip or the needle tip is disposed at or just proximal to the dilator tip. In this way, the stylet tip or the needle tip can be guarded so as to lessen the likelihood of inadvertently exposing the patient to the stylet tip or the needle tip. In some examples, referring to FIGS. 6A and 6B, the needle cannula 660 is inserted into the dilator 640 along arrows H. In some examples, the needle cannula 660 is placed in the desired location within the dilator 640. For instance, the desired location, in some examples, is the point within the dilator 640 at which the stylet tip is positioned at or just proximal to a dilator tip. In other examples, other positions of the stylet tip with respect to the dilator tip can be desirable.

Once the desired location of the needle cannula 660 within the dilator 640 is reached, referring to FIG. 6C, in some examples, the physician or other user can place the spacers 670 onto the needle cannula 660 such that the dilator 640 abutting or coupled to the distal-most spacer 670 positions the needle cannula within the desired location within the dilator 640. In some examples, positioning the adjustment assembly 610 in this way engages the needle cannula 660 to inhibit the stylet tip of the stylet 680 disposed within the lumen of the needle cannula 660 from inadvertently moving distally from the dilator tip. Referring to FIG. 6D, in some examples, once the stylet 680 is no longer needed for the procedure, the stylet 680 can be removed from within the needle cannula 660, for instance, by pulling the stylet 680 proximally out of the port 667. Once the stylet 680 is removed, in some examples, the first, distal-most spacer 670 can be removed along arrow I. With the spacer 670 removed, in some examples, the adjustable assembly 610 (for instance, the two remaining spacers 670) and the needle cannula 660 can be advanced distally along arrows J, as shown in FIG. 6E. In some examples, the first, distal-most spacer 670 is sized such that it maintains the stylet tip disposed within the dilator 640, and, with the removal of the spacer 670, distally advancing the needle cannula 660 and adjustable assembly 610 to close the gap left by the first, distal-most spacer 670 and abutting or coupling the dilator 540 to the next spacer 670 in line places the needle tip of the needle cannula 660 at or just proximal to the dilator tip.

The needle cannula 660 and the dilator 640 can then be placed in the desired location within the patient, for instance, with the dilator tip proximate or abutting the tissue layer desired to be punctured (in a manner similar to that which is shown in FIG. 8A). In some examples, with the dilator 640 rotatable with respect to the adjustable assembly 610, rotation of the needle cannula 660 with respect to the dilator 640 can be accomplished, for instance, to facilitate maneuvering of the dilator 640 and the needle cannula 660 to the desired location within the patient. Referring to FIG. 6F, in some examples, with the dilator 640 and the needle cannula 660 in the desired position for puncturing, the second, now-distal-most spacer 670 can be removed from the needle cannula 660 along arrow K. Referring to FIGS. 6G and 6H, in some examples, with the second spacer 670 removed, the needle cannula 660 and the adjustable assembly 610 can be distally advanced to close the gap left by the second spacer 670 to extend the needle tip distally from the dilator tip and puncture the tissue layer (in a manner similar to that which is shown in FIG. 8B). In this way, in some examples, the adjustable assembly 610 allows for puncturing of the tissue layer.

Figure 7A:
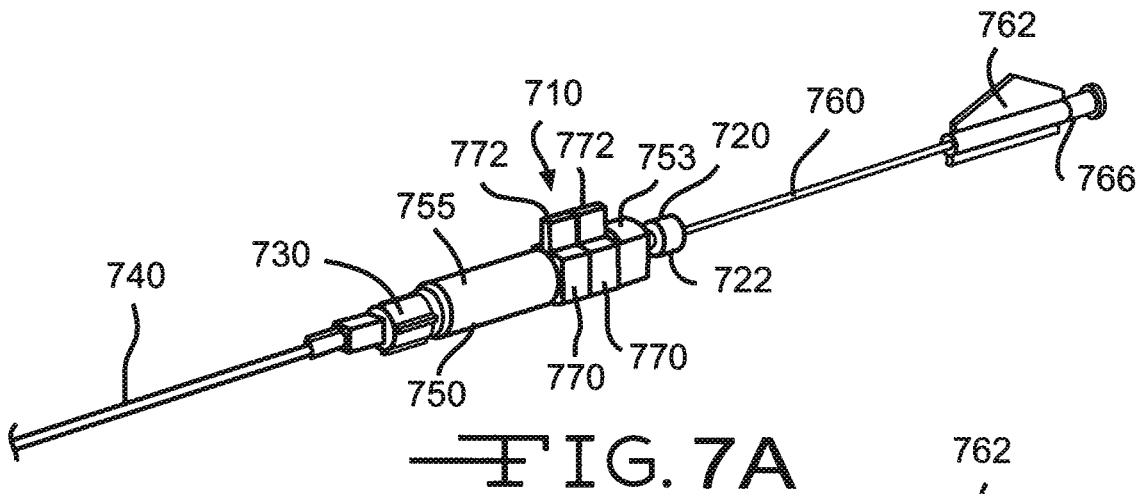
FIGS. 7A-7C are perspective views of an adjustable needle assembly in accordance with at least one example of the invention.
Figure 7B:
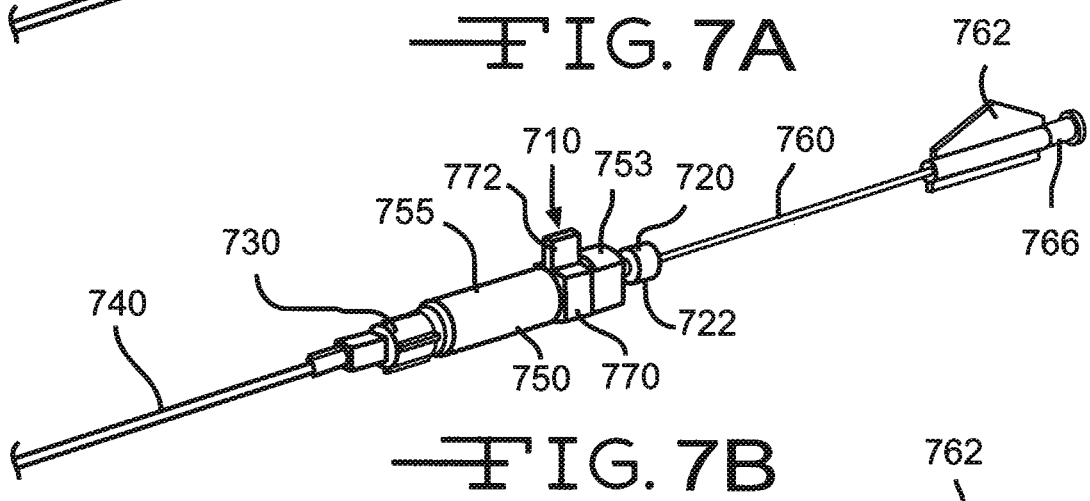
Figure 7C:
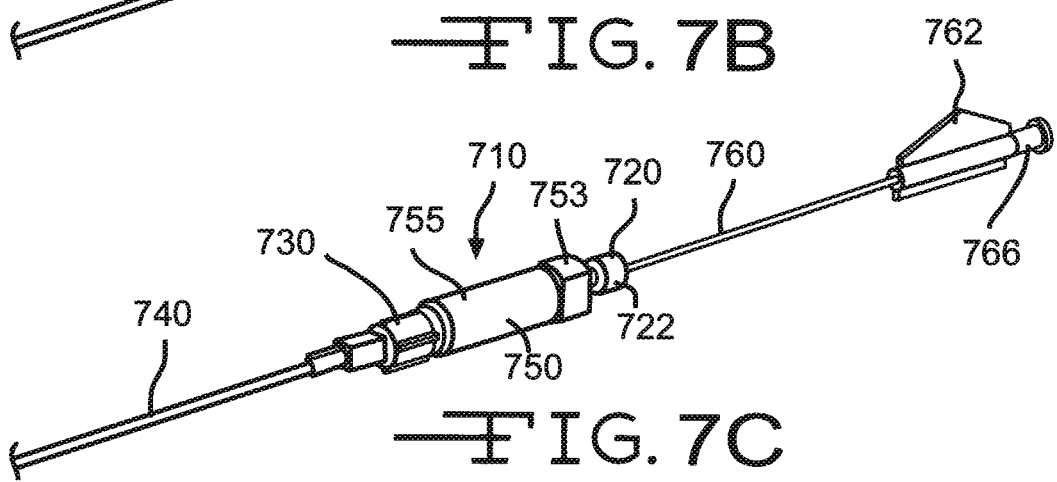

Referring to FIGS. 7A-7C, in some examples, an adjustable assembly 710 can be used, for instance, to position a stylet tip of a stylet or a needle tip of a needle assembly 760 with respect to a dilator 740. In other examples, the adjustable assembly 710 can be used to position other assemblies with respect to one another. In some examples, the adjustable assembly 710 is configured to adjustably anchor the adjustable assembly 710 and, in turn, the dilator 740 with respect to the needle cannula 760. In some examples, the needle cannula 760 includes a handle 762 engaged at a proximal end of the needle cannula 760 to facilitate the physician or other user in handling or maneuvering the needle cannula 760. In some examples, the handle includes a port 766 fluidly coupled to a lumen of the needle cannula 760 to which to attach a syringe (for injecting contrast material, for instance), a positive pressure source, a negative pressure source, or the like. In some examples, the port 766 includes a stopcock or other coupling assembly configured to selectively open or close the port 766. In some examples, the port 766 is configured to accept the stylet in order to insert the stylet within the lumen of the needle cannula 760. Although shown used with the needle cannula 760 and the handle 762 described herein, it is contemplated that the adjustable assembly 710 can be used with another needle cannula or another apparatus or assembly.

In some examples, the adjustable assembly 710 includes a gripping member 720. In some examples, the gripping member 720 includes a Tuohy-Borst valve. In some examples, the gripping member 720 can be similar to the gripping members 120, 220, 520 described herein. In some examples, the gripping member 720 includes an open configuration (for instance, with an outer portion 722 of the gripping member 720 rotated in a loosening direction to open a passage within the gripping member 720) and a closed configuration (for instance, with the outer portion 722 of the gripping member 720 rotated in a tightening direction, for instance, to close the passage within the gripping member 720 around the needle cannula 760).

In some examples, the adjustable assembly 710 includes a coupling member 730. In some examples, the coupling member 730 is rotatably attached with respect to the gripping member 720. In some examples, the coupling member 730 is configured to selectively couple with another member, such as, but not limited to, the dilator 740. In some examples, the coupling member 730 includes a Luer connector. In further examples, the coupling member 730 includes a male Luer portion configured to removably couple to a female Luer portion, for instance, a female Luer portion of the dilator 740. In other examples, the coupling member 730 is a type of connector other than a Luer connector, such as, but not limited to, a threaded coupling (other than a Luer connector), a snap fitting, a collet fitting, a magnetic coupling, or the like, for instance. In some examples, the coupling member 730 includes a bore, similar to the bore 132 of the adjustable assembly 110 described herein, fluidly coupled with the passage of the gripping member 720.

In some examples, the adjustable assembly 710 includes a puncture member 750. In some examples, the puncture member 750 is configured to selectively allow for puncturing of a tissue layer with a needle tip of the needle cannula 760 (in a manner similar to that which is shown in FIG. 8B). The puncture member 750, in some examples, is coupled to the gripping member 720 on one side and the coupling member 730 on the other side. In some examples, the coupling member 730 is rotatably attached to the puncture member 750. In some examples, the puncture member 750 fluidly couples the passage of the gripping member 720 and the bore of the coupling member 730 to allow the needle cannula 760 to extend through the adjustable assembly 710. In some examples, the puncture member 750 includes a first portion 753 attached to the gripping member 720. The puncture member 750, in some examples, includes a second portion 755 movable with respect to the first portion 753. In some examples, the first portion includes a shaft-like portion extending into the second portion 755. In some examples, the first portion 753 and second portion 755 form a piston-like assembly. In some examples, the second portion 755 is attached to the coupling member 730. In this way, in some examples, with the gripping member 720 engaged with the needle cannula 760 in the closed configuration and the dilator 740 coupled to the coupling member 730, movement of the first portion 753 with respect to the second portion 755 moves the needle cannula 760 with respect to the dilator 740. In this way, in some examples, a puncture of a tissue layer can be performed (similar to that which is shown in FIG. 8B) by moving the first portion 753 with respect to the second portion 755. In some examples, during the puncturing of the tissue layer, the second portion 755 and, in turn, the dilator 740, is substantially held stationary with respect to the patient and the first portion 753 and, in turn, the needle cannula 760 is advanced distally with respect to the dilator 740 to allow the needle tip to extend from the dilator and puncture the desired tissue layer. In other examples, the first portion 753 and, in turn, the needle cannula 760, can be substantially held stationary with respect to the patient and the second portion 755 and, in turn, the dilator 740 is advanced proximally with respect to the needle cannula 760.

In some examples, the adjustable assembly 710 includes one or more spacers 770 removably coupled between the first portion 753 and the second portion 755 of the puncture member 750. In some examples, the one or more spacers 770 are similar to the spacers 570, 670 described herein. In some examples, the one or more spacers 770 can be removably disposed on the first portion 753 to position the dilator 740 with respect to the needle cannula 760. The one or more spacers 770, in some examples, include a slot (similar to the slot 574 of the spacer 570 described herein) configured to selectively frictionally engage with the first portion 753. In this way, in some examples, the one or more spacers 770 can be selectively removed from the first portion 753 at which point the physician or other user desires to do so. In some examples, the one or more spacers 770 each include a tab 772 or other feature to facilitate grasping of the spacer 770 by the physician or other user, for instance, during removal of the spacer 770 from the first portion 753. In some examples, the one or more spacers 770 can be used to position the dilator 740 with respect to the needle cannula 160, for instance, to maintain the stylet tip of the stylet (extending distally from the needle tip of the needle cannula 660) within the dilator 740 or to maintain the needle tip of the needle cannula 760 within the dilator 740. In this way, in some examples, the stylet tip or the needle tip can be shielded to lessen the likelihood of inadvertent exposure of the patient to the stylet tip or needle tip. In some examples, the spacers 770 (if more than one spacer 770 are used) can interlock with or otherwise attach to one another. In further examples, the spacers 770 can interlock such that the spacers 770 can only be removed from the first portion 753 in a particular order. In some examples, with the one or more spacers 770 coupled between the first portion 753 and the second portion 755, movement of the first portion 753 with respect to the second portion 755 is inhibited.

In the examples described herein, the adjustable assembly 710 includes two spacers 770. It is contemplated, however, that in other examples, more or fewer than two spacers 770 can be used to accomplish one or more positioning of the dilator 740 with respect to the needle cannula 760.

Referring still to FIGS. 7A-7C, in operation, in some examples, the adjustable assembly 710 can be used to locate and retain the needle cannula 760 in a desired relationship with respect to the dilator 740. For instance, in a manner similar to that described herein and shown in FIG. 8A, in some examples, it can be desirable to position the needle cannula 760 within the dilator 740 such that the stylet tip or the needle tip is disposed at or just proximal to the dilator tip. In this way, the stylet tip or the needle tip can be guarded so as to lessen the likelihood of inadvertently exposing the patient to the stylet tip or the needle tip. In some examples, referring to FIG. 7A, the needle cannula 760 is inserted into the dilator 740 and the adjustable assembly 710 with the gripping member 720 in the open configuration. In some examples, the needle cannula 760 is placed in the desired location within the dilator 740. For instance, the desired location, in some examples, is the point within the dilator 740 at which the stylet tip is positioned at or just proximal to a dilator tip. In other examples, other positions of the stylet tip with respect to the dilator tip can be desirable.

Once the desired location of the needle cannula 760 within the dilator 740 is reached, in some examples, the physician or other user can place the gripping member 720 in the closed configuration (for instance, by rotating the outer portion 722 of the gripping member 720 in a tightening direction or by releasing one or more tabs of one or more wings to allow the one or more wings to return to the closed configuration with one or more surfaces of the one or more wings in frictional engagement with the needle cannula 760) to grip or otherwise compressively or frictionally engage the needle cannula 760 and inhibit movement of the adjustment assembly 710 and, in turn, the dilator tip of the dilator 740 with respect to the stylet tip and the needle cannula 760. In some examples, positioning the adjustment assembly 710 in this way engages the needle cannula 760 to inhibit the stylet tip of the stylet disposed within the lumen of the needle cannula 760 from inadvertently moving distally from the dilator tip. Referring to FIG. 7B, in some examples, once the stylet is no longer needed for the procedure, the stylet can be removed from within the needle cannula 760, for instance, by pulling the stylet proximally out of the port 766. Once the stylet is removed, in some examples, the first, distal-most spacer 770 can be removed from the adjustable assembly 710. With the first, distal-most spacer 770 removed, in some examples, the first portion 753 and the needle cannula 760 can be advanced distally. In some examples, the first, distal-most spacer 770 is sized such that it maintains the stylet tip disposed within the dilator 740, and, with the removal of the spacer 770, distally advancing the needle cannula 760 and the first portion 753 to close the gap left by the first, distal-most spacer 770 and abutting the remaining spacer 770 between the first portion 753 and the second portion 755 places the needle tip of the needle cannula 760 at or just proximal to the dilator tip.

The needle cannula 760 and the dilator 740 can then be placed in the desired location within the patient, for instance, with the dilator tip proximate or abutting the tissue layer desired to be punctured (in a manner similar to that which is shown in FIG. 8A). In some examples, with the dilator 740 rotatable with respect to the puncture assembly 750, rotation of the needle cannula 760 with respect to the dilator 740 can be accomplished, for instance, to facilitate maneuvering of the dilator 740 and the needle cannula 760 to the desired location within the patient. Referring to FIG. 7C, in some examples, with the dilator 740 and the needle cannula 760 in the desired position for puncturing, the remaining spacer 770 can be removed from the first portion 753. With the remaining spacer 770 removed, in some examples, the needle cannula 760 and the first portion 753 can be distally advanced to close the gap left by the second spacer 770 to extend the needle tip distally from the dilator tip and puncture the tissue layer (in a manner similar to that which is shown in FIG. 8B). In some examples, with the removal of the second spacer 770, the first portion 753 can abut the second portion 755 of the puncture member 750. In this way, in some examples, the adjustable assembly 710 allows for puncturing of the tissue layer.

The present inventors have recognized various advantages of the subject matter described herein. For instance, in some examples, the present subject matter can be used to selectively adjustably anchor a dilator with respect to a needle cannula in a procedure for puncturing a tissue layer, for instance, puncturing of a septal wall during transseptal catheterization. Such adjustable anchoring of the dilator with respect to the needle cannula can decrease the occurrence of inadvertent exposure of the patient to the needle tip. That is, the physician or other user can anchor the dilator with respect to the needle cannula to place and maintain the tip of the needle cannula within the dilator until the physician or other user is ready to perform the puncture. Moreover, allowing the dilator to be adjustably anchored to the needle cannula allows variously-sized dilators to be used with variously-sized needle cannulas, thereby lessening, if not eliminating, the need to use a specific size of dilator with a specific size of needle cannula. In some examples, allowing the dilator to be adjustably anchored to the needle cannula allows dilators of various lengths to be used with needle cannulas of various lengths, thereby lessening, if not eliminating, the need to use a specific length of dilator with a specific length of needle cannula. In this way, hospitals or other health care facilities can decrease the number and/or sizes or lengths of dilators and needle cannulas that are stocked. While various advantages of the example needle assemblies are listed herein, this list is not considered to be complete, as further advantages may become apparent from the description and figures presented herein.

Although the subject matter of the present patent application has been described with reference to various examples, workers skilled in the art will recognize that changes can be made in form and detail without departing from the scope of the subject matter recited in the below claims.

The above Detailed Description includes references to the accompanying drawings, which form a part of the Detailed Description. The drawings show, by way of illustration, specific examples in which the present apparatuses and methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" or similar are used to refer to an amount that is nearly, almost, or in the vicinity of being equal to a stated amount.

In the appended claims, the terms "including" and "in which" are used as the plain-English equivalents of the respective terms "comprising" and "wherein." Also, in the following claims, the terms "including" and "comprising" are open-ended, that is, an apparatus or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

The invention claimed is:

1. An apparatus comprising:
a gripping member including a body and a gripping portion attached to the body, the body including a passage configured to accept a needle cannula within and extending distally from the passage, the passage including a proximal opening, the gripping member including:
  an open configuration in which the needle cannula is movable within the passage; and
  a closed configuration in which the gripping portion is positioned to at least partially cover the proximal opening of the passage to directly frictionally contact a surface of the needle cannula proximal to the needle cannula surface being received in the passage of the body of the gripping member to thereby grip the needle cannula and inhibit movement of the needle cannula within the passage; and
a coupling member rotatably attached to the gripping member, the coupling member configured to selectively couple with a dilator, the coupling member including a bore fluidly coupled with the passage, the bore being configured to accept the needle cannula within the bore.

2. The apparatus of claim 1, wherein the gripping portion frictionally and compressively contacts the surface of the needle cannula in the closed configuration.

3. The apparatus of claim 1, wherein the gripping portion includes a wing movable with respect to the body, the wing movable between the open configuration and the closed configuration, the wing including a surface configured to directly frictionally contact the surface of the needle cannula in the closed configuration to inhibit movement of the needle cannula within the passage.

4. The apparatus of claim 1, wherein the gripping portion includes at least two wings movable with respect to the body, each of the wings movable between the open configuration and the closed configuration, each of the wings including a surface configured to directly frictionally contact the surface of the needle cannula in the closed configuration to inhibit movement of the needle cannula within the passage.

5. The apparatus of claim 4, wherein two of the at least two wings are diametrically opposed from one another.

6. The apparatus of claim 1, wherein the gripping member includes a Tuohy-Borst valve.

7. The apparatus of claim 1, comprising a puncture member including:
 a first portion attached to the gripping member; and
 a second portion movable with respect to the first portion, the second portion being attached to the coupling member, wherein, with the gripping member directly frictionally contacting the surface of the needle cannula in the closed configuration and the dilator coupled to the coupling member, movement of the first portion with respect to the second portion moves the needle cannula with respect to the dilator.

8. The apparatus of claim 7, wherein the puncture member includes:
 a potential energy storage member disposed between the first portion and the second portion; and
 an actuator operatively coupled to the potential energy storage member, wherein triggering of the actuator releases the potential energy storage member to move the first portion with respect to the second portion, wherein, with the gripping member directly frictionally contacting the surface of the needle cannula in the closed configuration and the dilator coupled to the coupling member, triggering of the actuator releases the potential energy storage member to move the needle cannula with respect to the dilator.

9. The apparatus of claim 8, wherein the potential energy storage member includes a spring.

10. The apparatus of claim 7, comprising a spacer removably coupled between the first portion and the second portion, wherein, with the spacer coupled between the first portion and the second portion, movement of the first portion with respect to the second portion is inhibited.

11. An apparatus comprising:
 a gripping member including a body and a gripping portion attached to the body, the body including a passage configured to accept a needle cannula within and extending distally from the passage, the passage including a proximal opening, the gripping member including:
  an open configuration in which the needle cannula is movable within the passage; and
  a closed configuration in which the gripping portion is positioned to at least partially cover the proximal opening of the passage to directly frictionally contact a surface of the needle cannula proximal to the needle cannula surface being received in the passage of the body of the gripping member to thereby grip the needle cannula and inhibit movement of the needle cannula within the passage; and
 a dilator rotatably attached to the gripping member, the dilator including a lumen fluidly coupled with the passage, the lumen being configured to accept the needle cannula within the lumen.

12. The apparatus of claim 11, wherein the gripping portion frictionally and compressively contacts the surface of the needle cannula in the closed configuration.

13. The apparatus of claim 11, wherein the gripping portion includes a wing movable with respect to the body, the wing movable between the open configuration and the closed configuration, the wing including a surface configured to directly frictionally contact the surface of the needle cannula in the closed configuration to inhibit movement of the needle cannula within the passage.

14. The apparatus of claim 11, wherein the gripping portion includes at least two wings movable with respect to the body, each of the wings movable between the open configuration and the closed configuration, each of the wings including a surface configured to directly frictionally contact the surface of the needle cannula in the closed configuration to inhibit movement of the needle cannula within the passage.

15. The apparatus of claim 14, wherein two of the at least two wings are diametrically opposed from one another.

16. The apparatus of claim 11, comprising a puncture member including:
 a first portion attached to the gripping member;
 a second portion movable with respect to the first portion, the second portion being attached to the dilator;
 a potential energy storage member disposed between the first portion and the second portion; and
 an actuator operatively coupled to the potential energy storage member, wherein triggering of the actuator releases the potential energy storage member to move the first portion with respect to the second portion, and, in turn, to move the needle cannula with respect to the dilator.

17. The apparatus of claim 16, wherein the potential energy storage member includes a spring.

18. An apparatus comprising:
 a gripping member including a body and a gripping portion attached to the body, the body including a passage configured to accept a needle cannula within and extending distally from the passage, the passage including a proximal opening, the gripping member including:
  an open configuration in which the needle cannula is movable within the passage; and
  a closed configuration in which the gripping portion is positioned to at least partially cover the proximal opening of the passage to directly frictionally contact a surface of the needle cannula proximal to the needle cannula surface being received in the passage of the body of the gripping member to thereby grip the needle cannula and inhibit movement of the needle cannula within the passage; and
 a puncture member including:
  a first portion attached to the gripping member;
  a second portion movable with respect to the first portion;
  a potential energy storage member disposed between the first portion and the second portion; and
  an actuator operatively coupled to the potential energy storage member, wherein triggering of the actuator releases the potential energy storage member to move the first portion with respect to the second portion.

19. The apparatus of claim 18, comprising a coupling member rotatably attached to the gripping member, the coupling member configured to selectively couple with a dilator, the coupling member including a bore fluidly coupled with the passage, the bore being configured to accept the needle cannula within the bore, wherein, with the gripping member directly frictionally contacting the surface of the needle cannula in the closed configuration and the dilator coupled to the coupling member, triggering of the actuator releases the potential energy storage member to move the needle cannula with respect to the dilator.

20. The apparatus of claim 18, comprising a dilator rotatably attached to the gripping member, the dilator including a lumen fluidly coupled with the passage, the lumen being configured to accept the needle cannula within the lumen, wherein triggering of the actuator releases the potential energy storage member to move the needle cannula with respect to the dilator.

* * * * *